(12) United States Patent
Heaney et al.

(10) Patent No.: US 7,875,069 B2
(45) Date of Patent: Jan. 25, 2011

(54) STENT WITH SUPPORT ELEMENT

(75) Inventors: Barry Heaney, Ballybrit (IE); Dave McMorrow, Fort Lorrenzo (IE); Anthony Malone, Oranhill (IE); Aiden Flanagan, Kilcolgan (IE); Tim O'Connor, Claragalway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 831 days.

(21) Appl. No.: 11/526,278

(22) Filed: Sep. 21, 2006

(65) Prior Publication Data
US 2008/0077230 A1 Mar. 27, 2008

(51) Int. Cl.
*A61F 2/06* (2006.01)
(52) U.S. Cl. ..................... 623/1.15; 623/1.32
(58) Field of Classification Search ........................ None
See application file for complete search history.

(56) References Cited

U.S. PATENT DOCUMENTS

| | | | |
|---|---|---|---|
| 5,766,240 A * | 6/1998 | Johnson ..................... 623/2.39 |
| 5,891,108 A | 4/1999 | Leone et al. |
| 6,071,305 A | 6/2000 | Brown et al. |
| 6,096,070 A | 8/2000 | Ragheb et al. |
| 6,190,404 B1 * | 2/2001 | Palmaz et al. .............. 623/1.15 |
| 6,200,341 B1 * | 3/2001 | Jones et al. ................ 623/2.39 |
| 6,241,762 B1 | 6/2001 | Shanley |
| 6,273,908 B1 | 8/2001 | Ndondo-Lay |
| 6,273,913 B1 | 8/2001 | Wright et al. |
| 6,287,628 B1 | 9/2001 | Hossainy et al. |
| 6,340,367 B1 * | 1/2002 | Stinson et al. ............. 623/1.34 |
| 6,395,326 B1 | 5/2002 | Castro et al. |
| 6,491,666 B1 | 12/2002 | Santini, Jr. et al. |
| 6,491,720 B1 * | 12/2002 | Vallana et al. ............. 623/1.42 |
| 6,558,422 B1 | 5/2003 | Baker et al. |
| 6,638,302 B1 | 10/2003 | Curcio et al. |
| 6,699,275 B1 * | 3/2004 | Knudson et al. ........... 623/1.12 |
| 6,709,379 B1 | 3/2004 | Brandau et al. |
| 6,770,089 B1 * | 8/2004 | Hong et al. ................ 623/1.16 |
| 6,887,266 B2 * | 5/2005 | Williams et al. ........... 623/1.16 |
| 6,979,347 B1 | 12/2005 | Wu et al. |
| 7,625,403 B2 * | 12/2009 | Krivoruchko .............. 623/2.17 |
| 2002/0038146 A1 | 3/2002 | Harry |
| 2002/0082680 A1 | 6/2002 | Shanley |
| 2003/0065381 A1 * | 4/2003 | Solar et al. ................. 623/1.15 |
| 2004/0117005 A1 * | 6/2004 | Nagarada Gadde et al. 623/1.42 |
| 2005/0137682 A1 * | 6/2005 | Justino ....................... 623/1.24 |
| 2005/0283225 A1 * | 12/2005 | Klisch ........................ 623/1.15 |
| 2006/0089704 A1 * | 4/2006 | Douglas ..................... 623/1.12 |
| 2007/0244545 A1 * | 10/2007 | Birdsall et al. ............. 623/1.26 |

FOREIGN PATENT DOCUMENTS

DE   EP1656905   *   5/2006
EP   1656905       5/2006

* cited by examiner

*Primary Examiner*—Corrine M McDermott
*Assistant Examiner*—Rebecca Straszheim
(74) *Attorney, Agent, or Firm*—Vidas, Arrett & Steinkraus P.A.

(57) ABSTRACT

An implantable stent comprising a first strut having an abluminal surface, and subluminal surface, and at least one side surface; a first depression formed in the abluminal surface; and a first support element at least partially disposed in the first depression; wherein at least a portion of the first support element extends beyond the abluminal surface of the first strut.

49 Claims, 16 Drawing Sheets

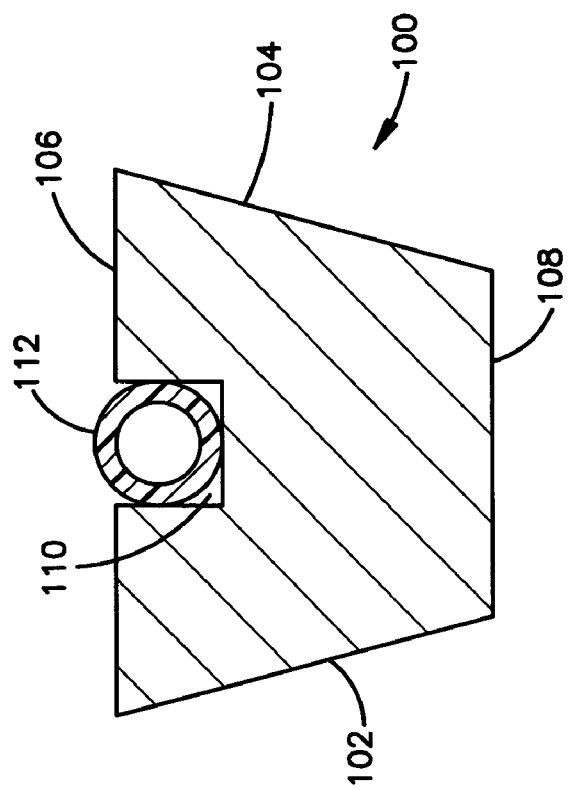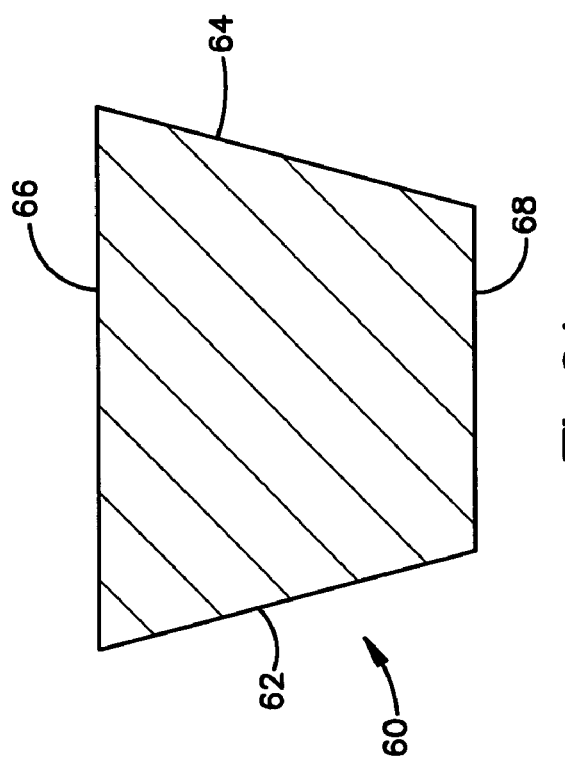

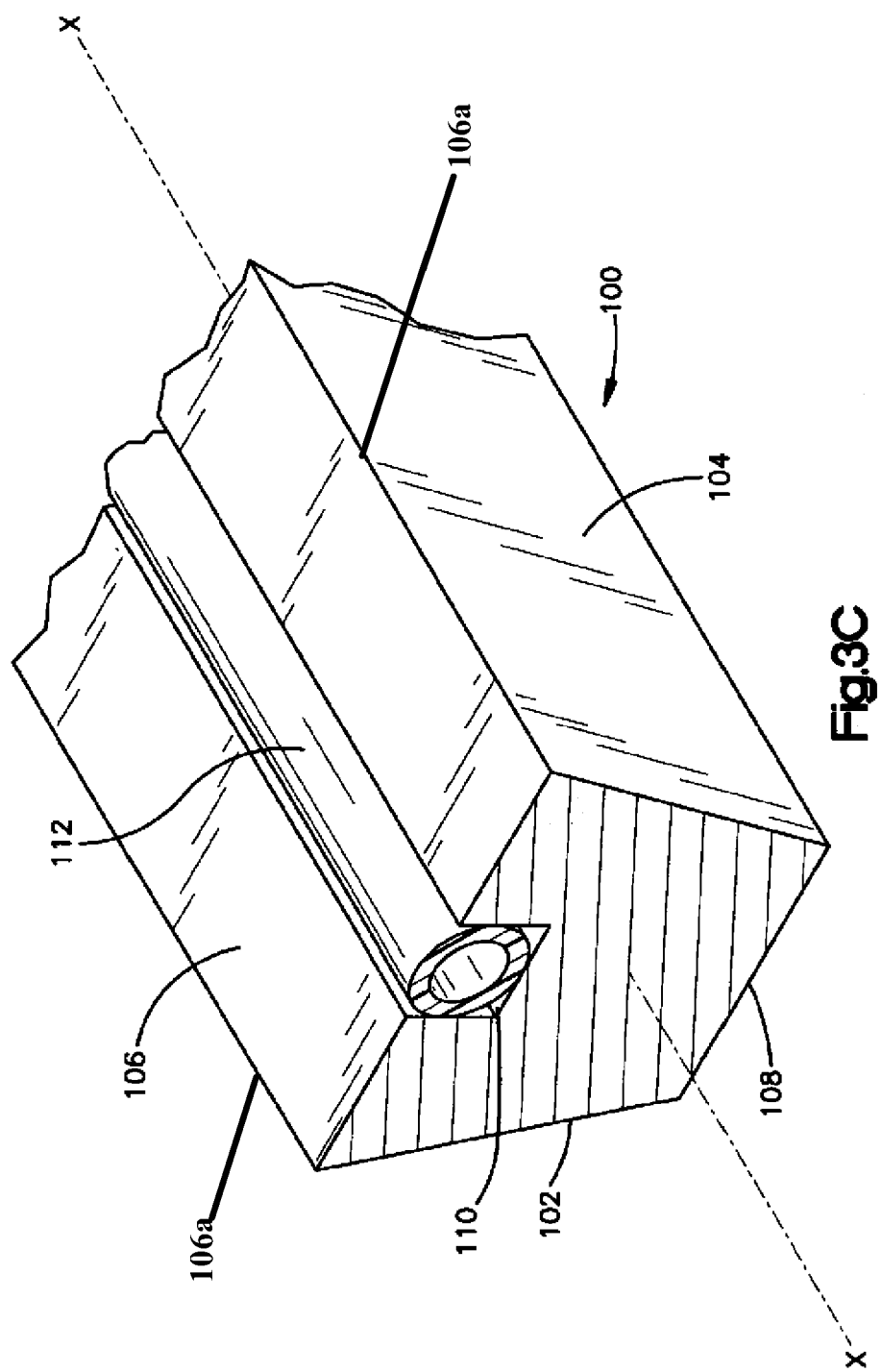

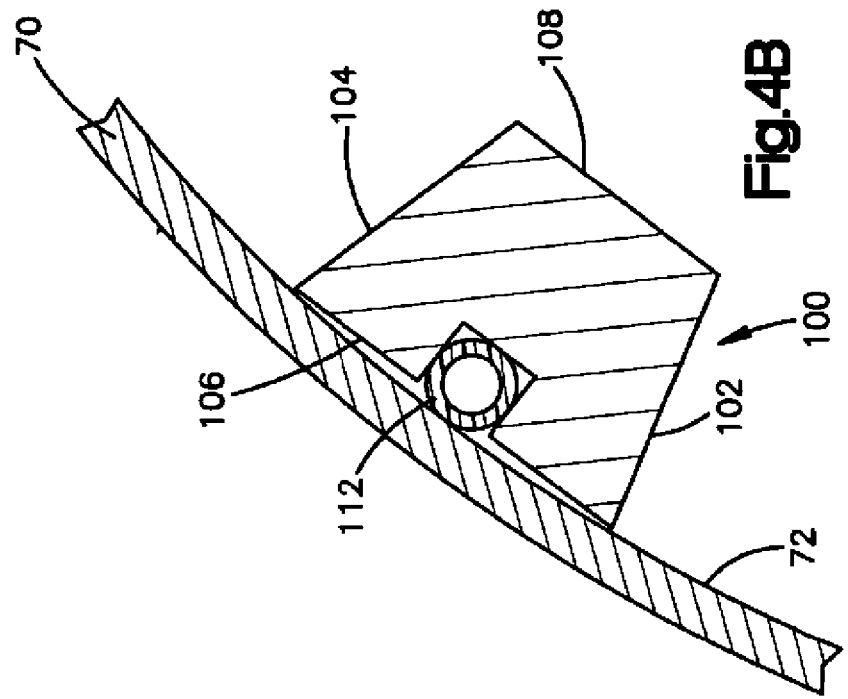
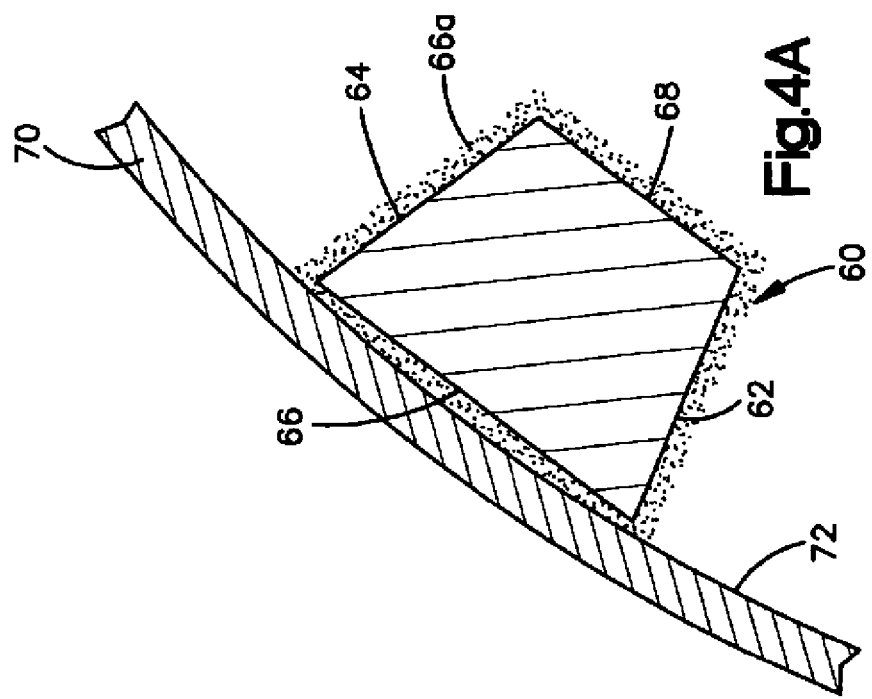

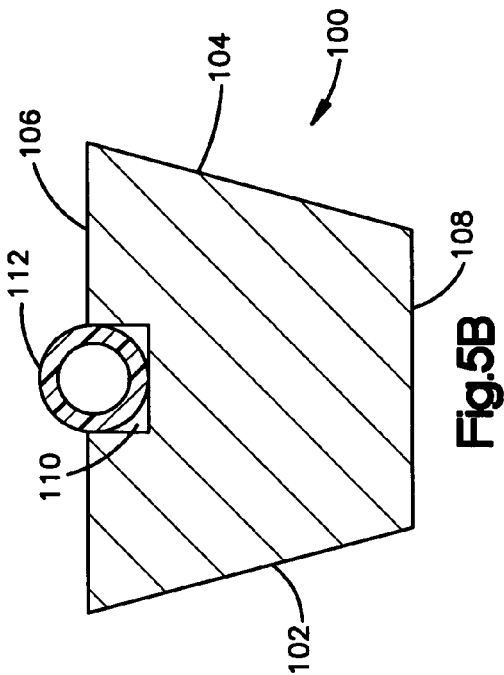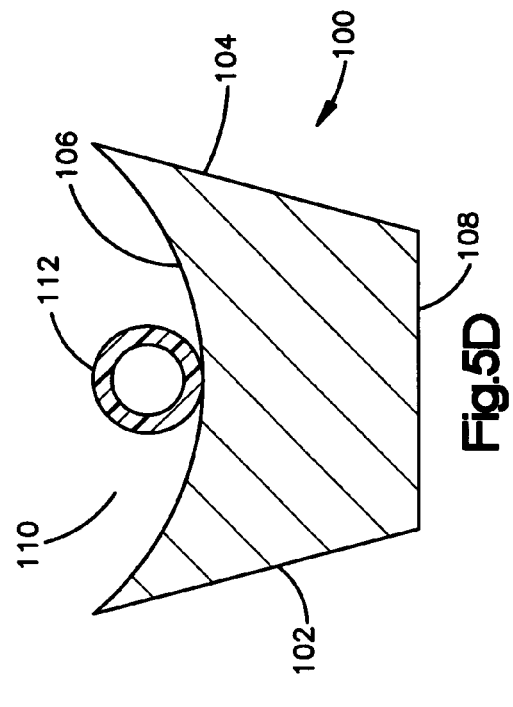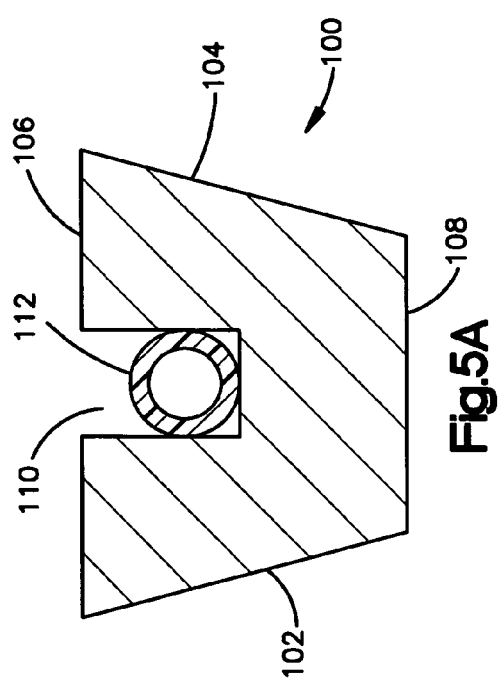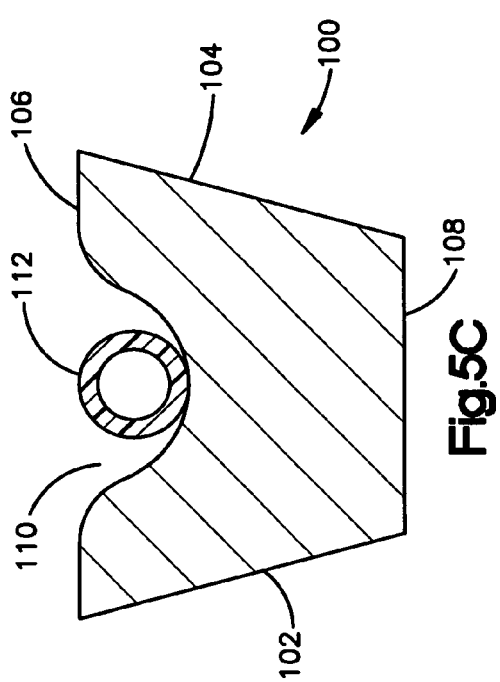

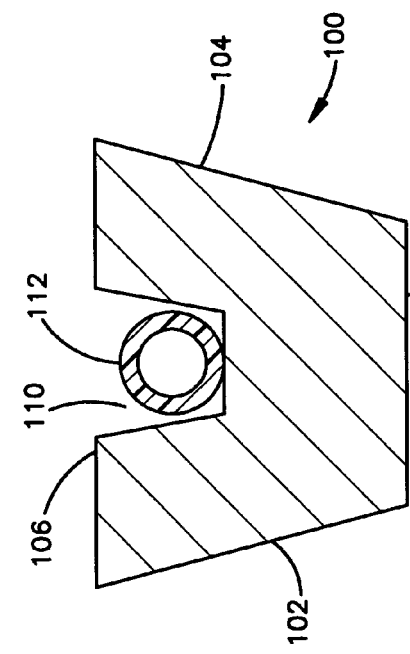
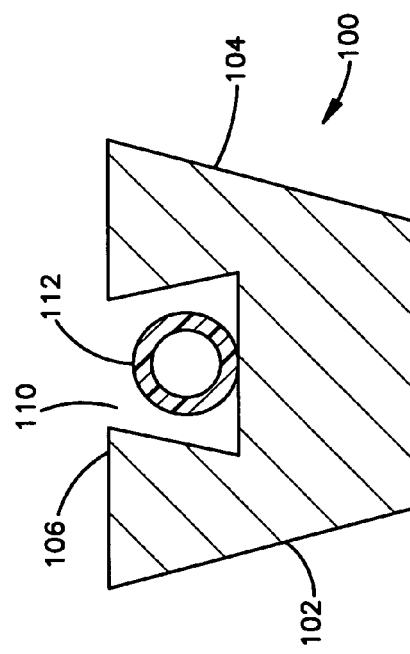
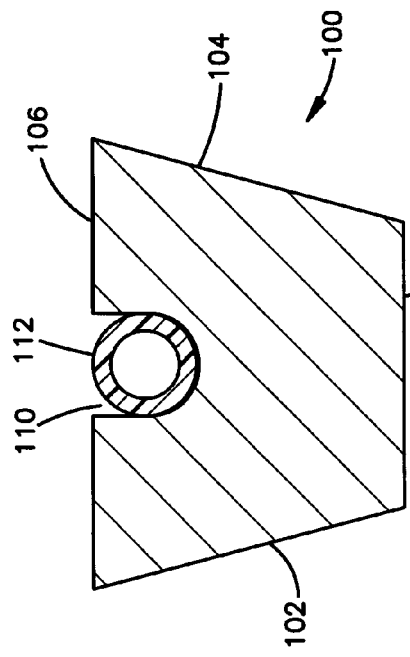
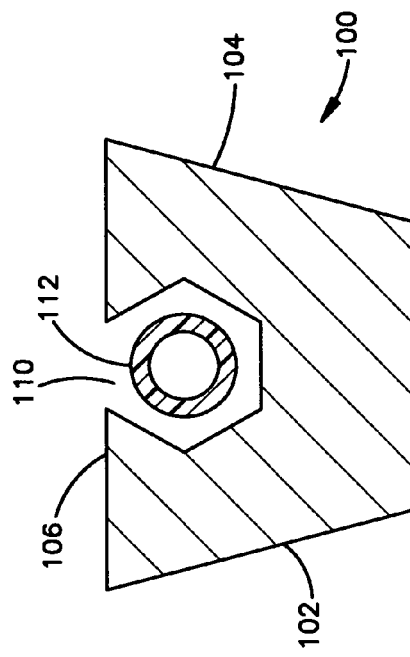

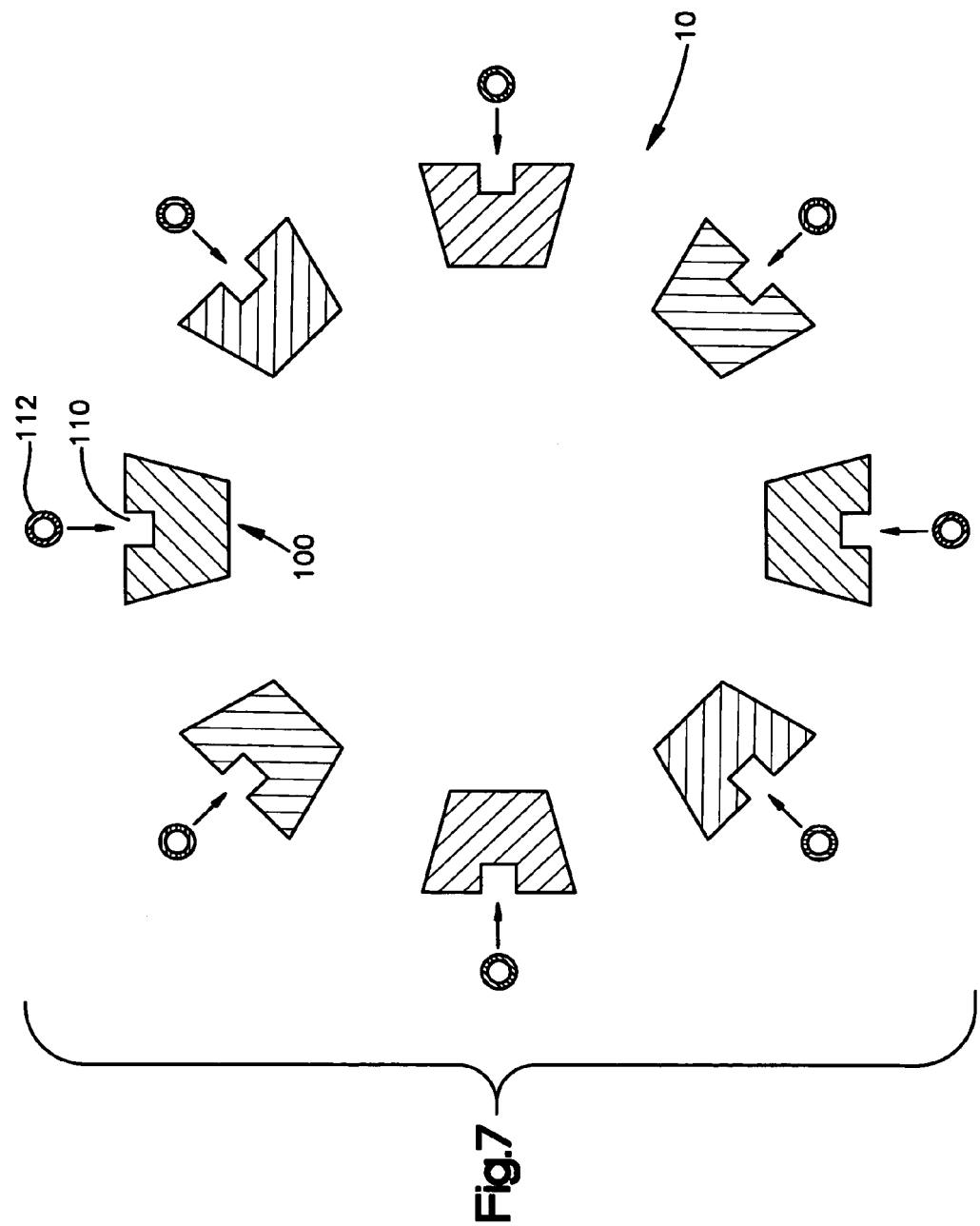

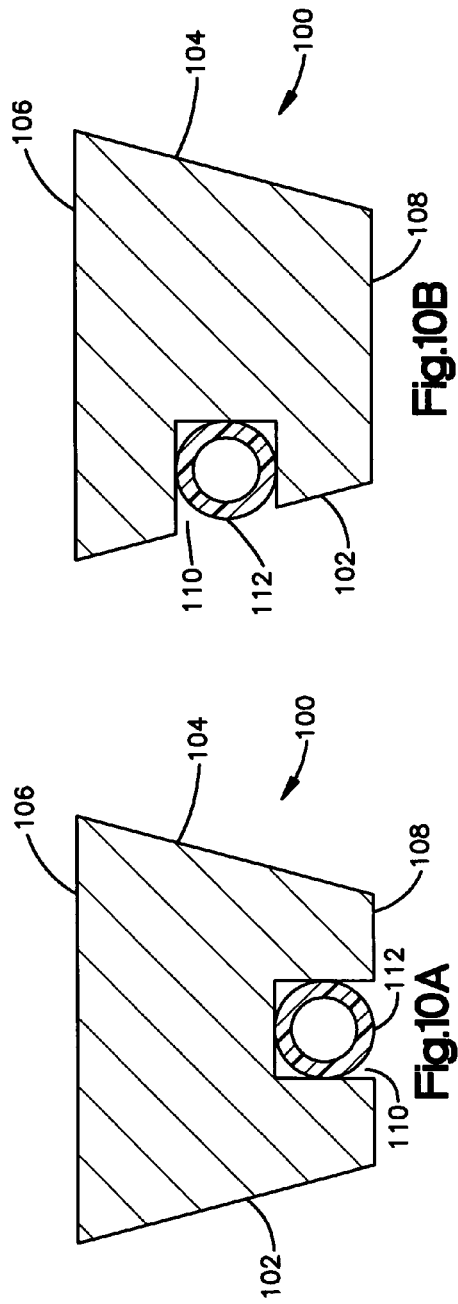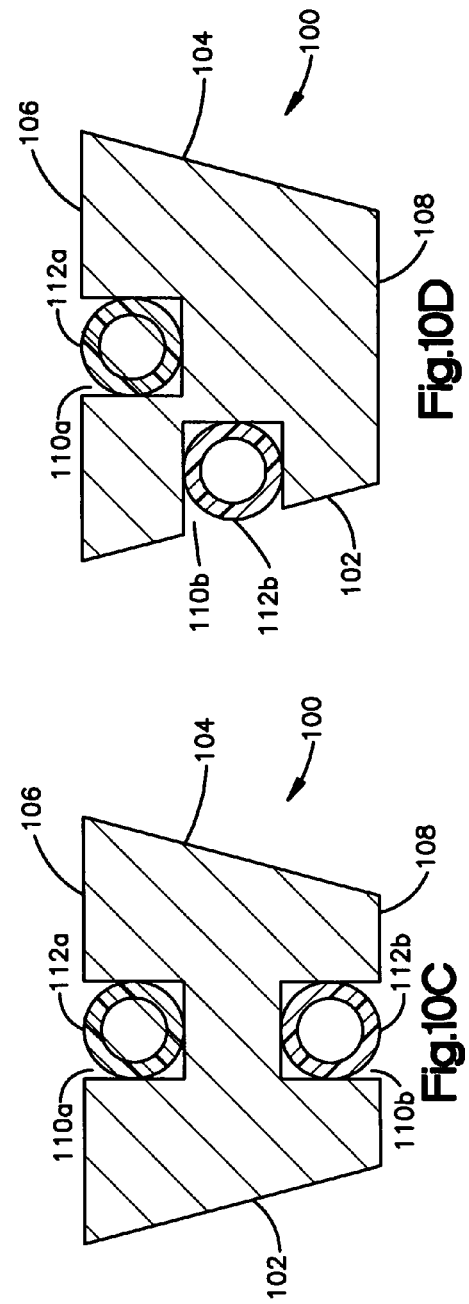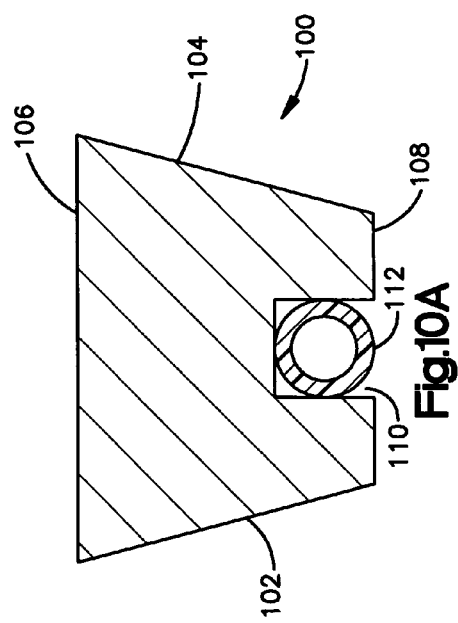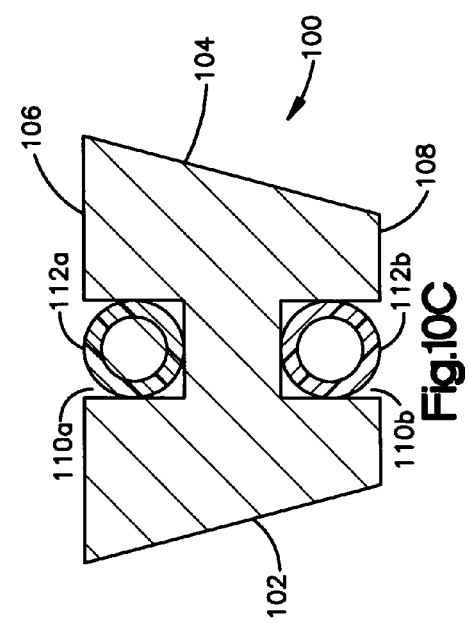

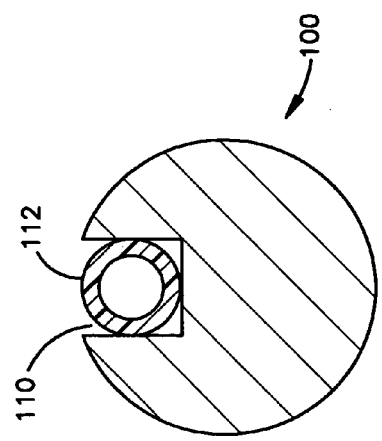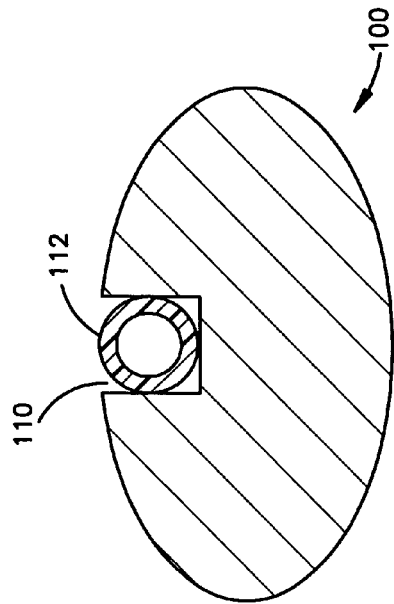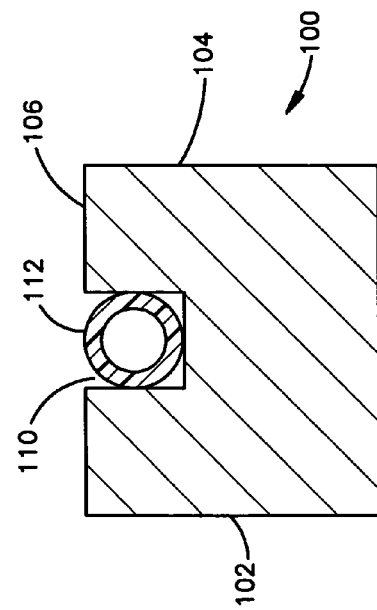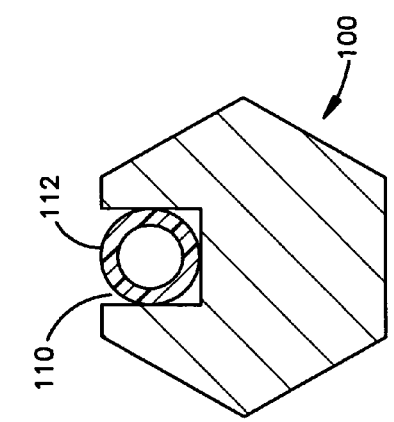

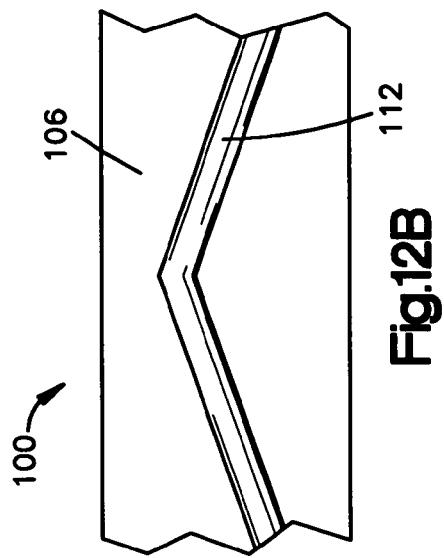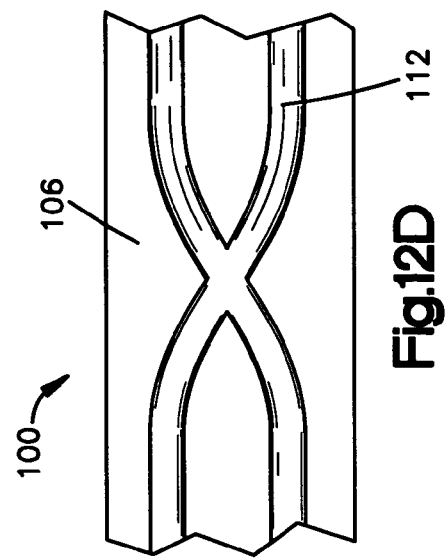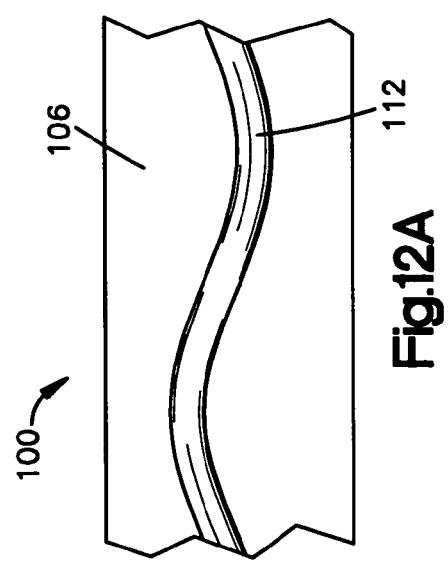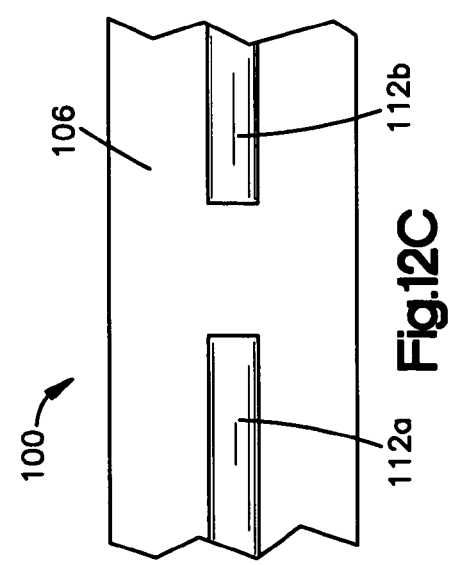

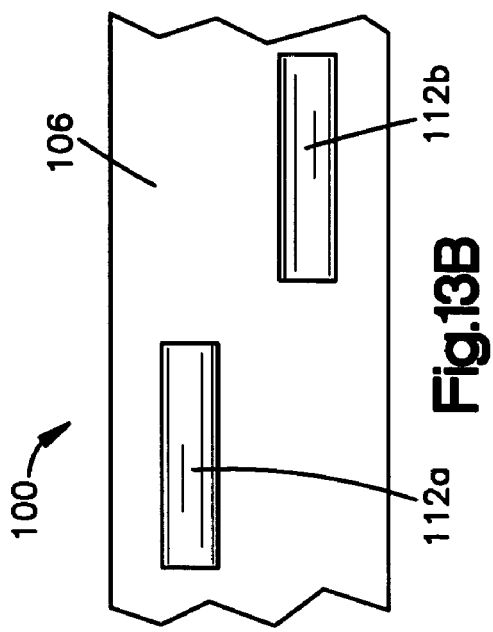
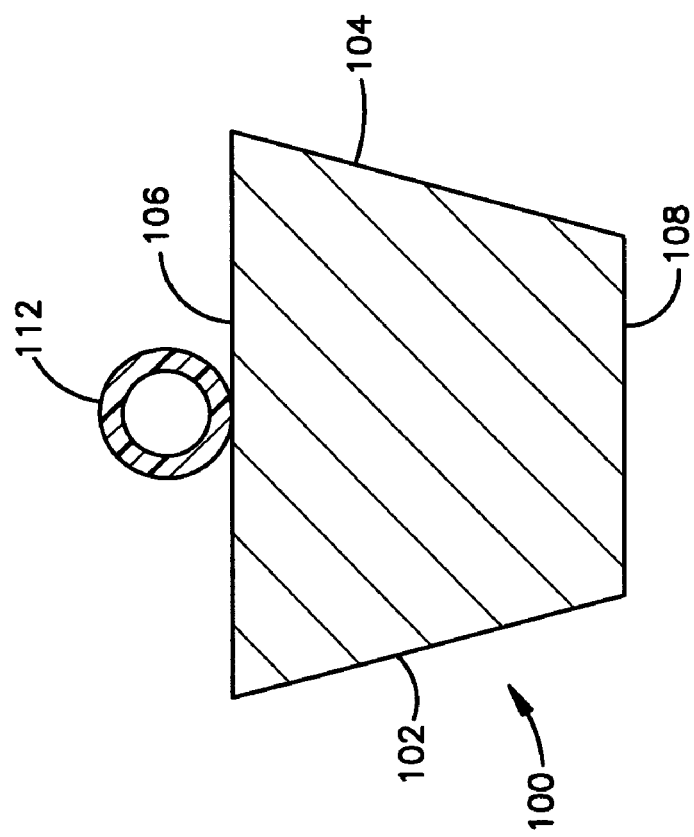

STENT WITH SUPPORT ELEMENT

FIELD OF THE INVENTION

This invention relates generally to medical devices, such as stents, for delivering a therapeutic agent to body tissue of a patient, such as a body lumen. More particularly, the invention is directed to a stent having a support element. The invention is also directed to a method for delivering therapeutic agents to body tissue of a patient.

BACKGROUND OF THE INVENTION

A variety of medical conditions have been treated by introducing an insertable medical device having a coating for release of a therapeutic agent. For example, various types of medical devices coated with a therapeutic agent, such as stents, have been proposed for localized delivery of such agents to a body lumen. See, e.g., U.S. Pat. No. 6,099,562 to Ding et al. issued on Aug. 8, 2000. However, it has been noted that therapeutic agent delivery by means of medical devices can be improved.

At present, many medical devices used for delivery a therapeutic agent to a body site are simply coated with a coating material, and may be fully encapsulated by the material. In the field of stents, the struts of the stent are typically sprayed with a polymer/therapeutic agent mix. There are, however, several drawbacks that may accompany full encapsulation of stent struts, including (1) an undue increase in effective stent strut profile; (2) the perhaps unwanted presence of a therapeutic agent on the inner surface (or subluminal surface) or strut side surfaces of the stent (where the agent may not provide a therapeutic benefit); (3) an increase in the likelihood that the total amount of therapeutic agent on the stent is greater than is needed (as a significant amount of the coating may simply serve to provide mechanical anchorage of the coating to the stent); (4) an increase in the balloon withdrawal forces because of friction between the balloon and the stent coating; and (5) the trade-offs that occur in selecting a therapeutic agent that is efficacious but durable.

Another approach used with medical devices for delivery of a therapeutic agent is to coat the stent abluminally, wherein the coating is applied only on the outer surface (or abluminal surface) of the device. In the field of stents, coatings on only the abluminal surface may also present drawbacks, however, including (1) the fact that very few effective coating methods are known which can enable deposition of precise quantities of coating on the abluminal surface of a stent; (2) precise coating methods are generally very time-consuming and may not lend themselves to commercial process scale-up; (3) as the success of abluminal coating may depend on the adhesion of the coating to the stent surface, this may unduly limit the range of materials that may be utilized; and (4) an undue increase in effective stent strut profile. Moreover, coating a stent abluminally may require the use of a polymer, which may be used to modulate therapeutic agent release over a period of time, but which may also have drawbacks relating to thrombosis concerns. However, coating a stent abluminally without the use of a polymer may result in a therapeutic agent release rate that is too high, and/or may result in ineffective coating adhesion to the stent.

Thus, there is a need for a medical device such as a stent with support elements that overcomes the above, and other, drawbacks.

SUMMARY OF THE INVENTION

A medical device, preferably a stent, comprising support elements disposed in at least one strut addresses these needs. The support element is preferably coated with a therapeutic agent, and preferably extends beyond the outer surface of a stent strut. Such a device has the advantages of being sufficiently mechanically strong, while also being able to effectively deliver a therapeutic agent to a body site.

An implantable stent is described comprising a stent sidewall having a plurality of struts including a first strut having an abluminal surface, a subluminal surface, and at least one side surface; a first depression formed in the abluminal surface of the first strut; and a first support element at least partially disposed in the first depression; wherein the first support element at least partially comprises a metal filament.

At least a portion of the first support element may extend beyond the abluminal surface of the first strut. The first depression may be a groove. The first support element may comprise a coating composition disposed thereon and wherein the coating composition may comprise a therapeutic agent. The coating composition may further comprise a polymer.

The first support element may have a curved cross-section. The first strut may comprise a coating composition disposed thereon. The stent may further comprise a second depression formed in the subluminal surface of the first strut; and a second support element at least partially disposed in the second first depression, and wherein the second support element at least partially comprises a metal filament. The stent of may further comprise a second strut having an abluminal surface and a second depression formed in the abluminal surface of the second strut.

The first support element may comprises a resilient metal, a shape-memory metal, and/or nitinol. The stent may be an intravascular stent.

Another implantable stent is described comprising a first strut having an abluminal surface, a subluminal surface, at least one side surface, and a longitudinal axis, a first depression formed in the abluminal surface of the first strut, wherein the first depression is disposed substantially parallel to the longitudinal axis of the first strut; and a first support element comprising a filament, wherein the first support element is at least partially disposed in the first depression. The first support element may be disposed substantially parallel to the longitudinal axis of the first strut.

Yet another implantable stent is described comprising a stent sidewall having a plurality of struts and openings therein, wherein, the sidewall comprises a first strut having an abluminal surface, a subluminal surface, and at least one side surface; a first depression formed in the abluminal surface of the first strut; and a first support element at least partially disposed in the first depression and wherein the first support element does not extend into any opening.

A method of manufacturing an implantable stent is described comprising providing a stent having a first strut; forming a first depression in the first strut; positioning a first support element adjacent the first depression; and allowing the first support element to contract such that at least a portion of the first support element is located in the first depression.

The first support element may be in expanded condition. The method may further comprise the step of at least partially coating the first support element with a coating composition comprising a therapeutic agent. The first depression may be formed using a laser.

A further method of manufacturing an implantable stent is described providing a stent having a first strut and a first depression; providing a first support element; positioning the first support element adjacent the first depression; and allowing the first support element to contract such that at least a portion of the first support element is located in the first depression.

BRIEF DESCRIPTION OF THE DRAWINGS

Preferred features of the present invention are disclosed in the accompanying drawings, wherein similar reference characters denote similar elements throughout the several views, and wherein:

FIG. 3A is a cross-sectional view of an exemplary stent strut;

FIG. 3B is a cross-sectional view of a strut having a support element;

FIG. 3C is a perspective view of a strut having a support element;

FIG. 4A is a cross-sectional view of the strut of FIG. 3A deployed adjacent a body lumen;

FIG. 4B is a cross-sectional view of the strut with support element of FIG. 3B deployed adjacent a body lumen;

FIGS. 5A-5H are cross-sectional views of various embodiments of struts having at least one support element;

FIGS. 6A-6D are cross-sectional views of various embodiments of struts having support elements disposed in depressions of various shapes;

FIG. 7 is an end view of a stent surrounded by an expanded support element system, prior to insertion of the support elements in the depressions

FIGS. 10A-10D are cross-sectional views of various embodiments of struts having at least one support element at various locations on the strut;

FIGS. 11A-11D are cross-sectional views of various embodiments of struts having various cross-sectional shapes having a support element;

FIGS. 12A-12D are top views of various embodiments of a strut having at least one support element;

FIG. 13A is a cross-sectional view of yet another embodiment of a strut having a support element; and FIG. 13B is a top view of an exemplary strut having the support element of FIG. 12A.

DETAILED DESCRIPTION OF THE PREFERRED EMBODIMENTS

Figure 1A:
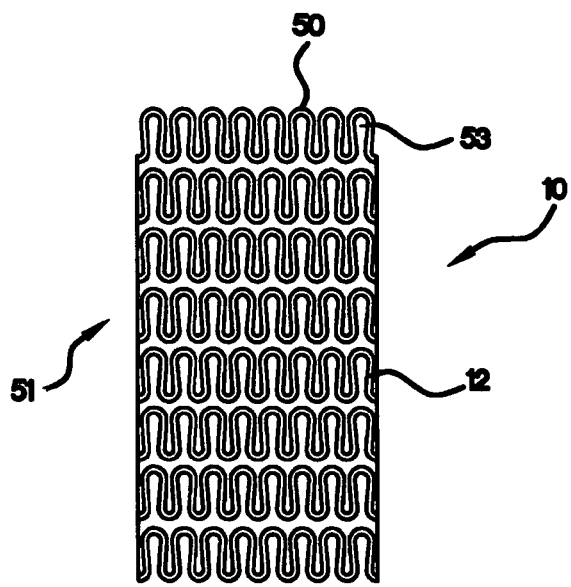
FIGS. 1A-1C are views of exemplary stents suitable for the present invention.
Figure 1B:
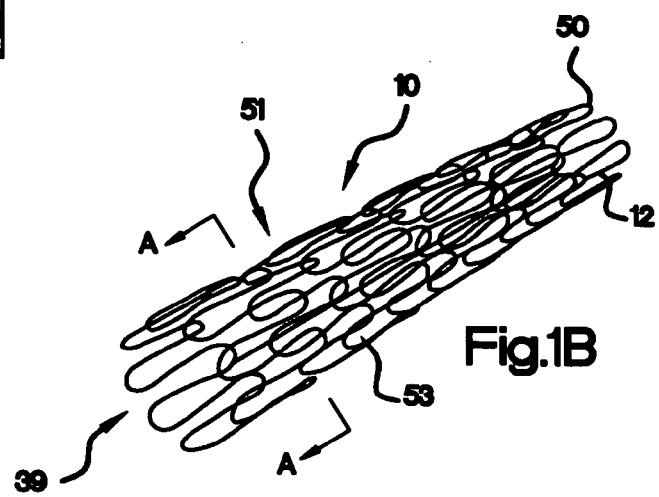
Figure 1C:
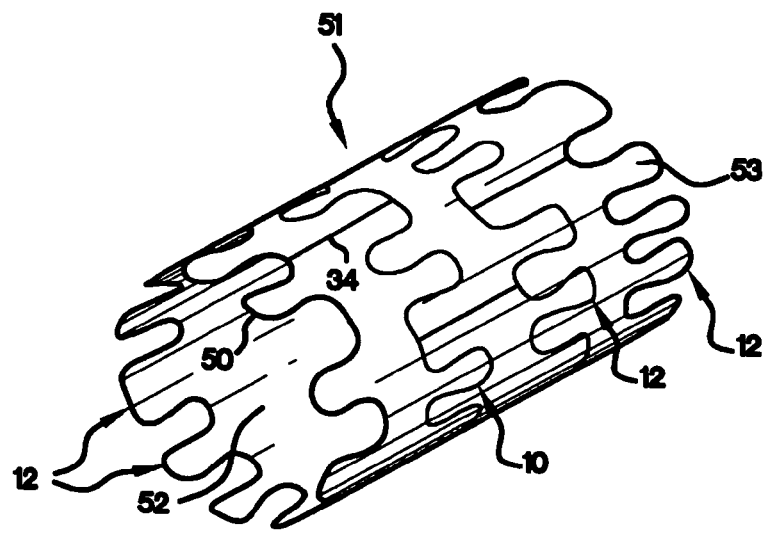

FIGS. 1A-1C show exemplary embodiments of a stent 10 that is suitable for use in the present invention. The stent 10 may have a flow path 52 therethrough and a stent sidewall 51 having a plurality of struts 50 and openings 53 in the sidewall. Stent 10 may also comprise a plurality of radially expandable cylindrical elements, and further may generally comprise struts 50 having a "peak" and "trough" configuration to form alternating loops. Adjacent radially expandable cylindrical elements 12 may be formed if at least two struts 50 are be connected to at least one connecting element 34. The connecting elements may be configured and situated to increase stability and/or flexibility of the stent. A more detailed discussion of stent configuration can be seen, inter alia, in U.S. Pat. No. 6,478,816 to Kveen et al., for "Stent", issued on Nov. 12, 2002, incorporated herein by reference in its entirety. Although the struts in this stent are shown to have a sinusoidal configuration, the struts can be straight. Generally, struts are wire-like elements or bar-like elements that make up a stent. The stent may have a substantially tubular shape.

Other suitable stents include, for example, intravascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

Stents that are suitable for the present invention may be fabricated from metallic, ceramic, or polymeric materials, or a combination thereof. Metallic materials are more preferable. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646.

Suitable ceramic materials include, but are not limited to, oxides, carbides, or nitrides of the transition elements such as titaniumoxides, hafnium oxides, iridiumoxides, chromium oxides, aluminum oxides, and zirconiumoxides. Silicon based materials, such as silica, may also be used.

The polymer(s) useful for forming the stent should be ones that are biocompatible and avoid irritation to body tissue. They can be either biostable or bioabsorbable. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for stents include without limitation dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly(γ-caprolactone), poly(γ-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of cells and molecules, such as proteins, nucleic acids, and the like.

Suitable stents may also be coated or made with non-polymeric materials. Examples of useful non-polymeric materials include sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; sphingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monoglycerides.

FIGS. 2A-2D show an exemplary delivery of a stent 10 into a body lumen. Stent 10 may first be mounted onto an inflatable balloon 14, or other mechanical delivery system, on the distal end of a delivery catheter 11. Stent 10 may be crimped or collapsed in substantially congruent dimensions to balloon 14. Guidewire 20 may be coaxially disposed in the body lumen prior to the introduction of the stent 10. Stent 10 and catheter 11 may then be introduced into a patient's body by methods such as the Seldinger technique, or other useful methods. Stent 10 and catheter 20 may be advanced over guidewire 20, at least to the area of obstruction 42. It may be preferable to advance the stent 10 until it is substantially centered in the area of obstruction 42 (see FIG. 2A).

Figure 2A:
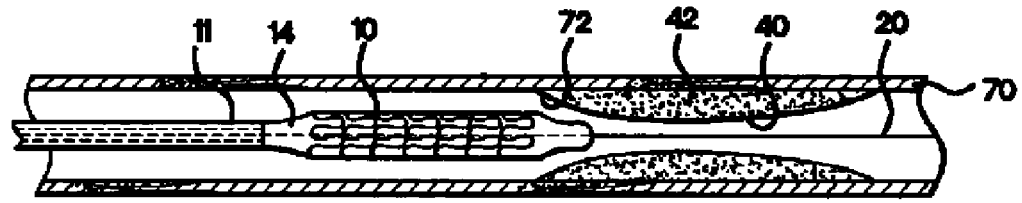
FIG. 2A is a top view, partially in section, of an exemplary stent in an unexpanded state within a body lumen, adjacent to a target tissue site.
Figure 2B:
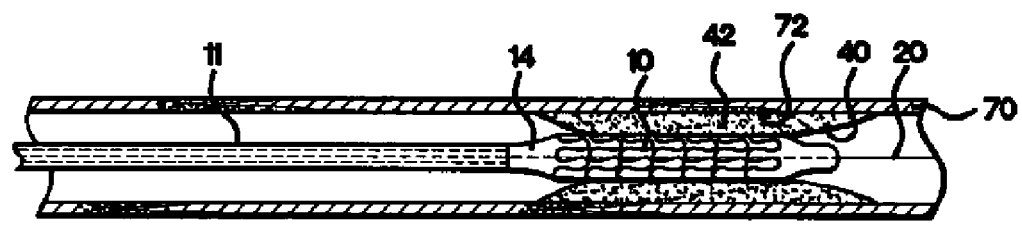
FIG. 2B is a top view, partially in section, of the configuration of FIG. 2A, wherein the unexpanded stent is positioned at the target tissue site.
Figure 2C:
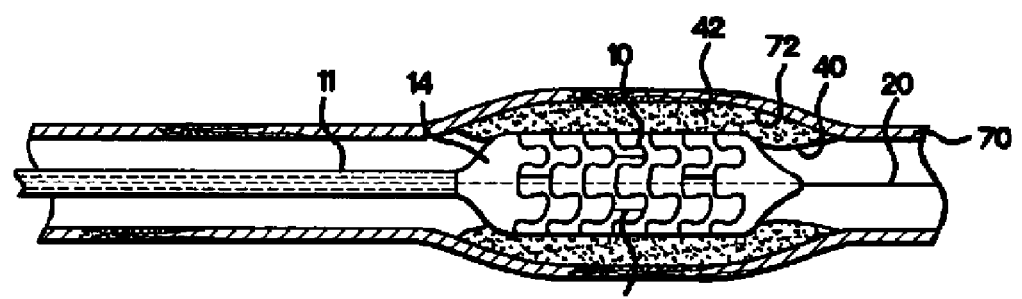
FIG. 2C is a top view, partially in section, of the configuration of FIG. 2B, wherein the stent is expanded and the struts are in contact with the target tissue site.
Figure 2D:
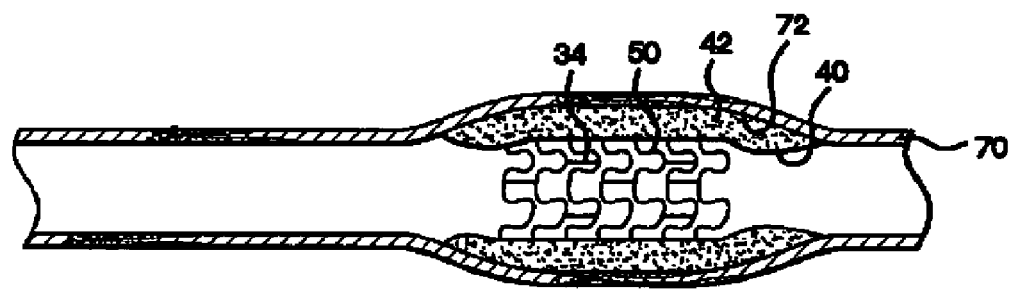
FIG. 2D is a top view, partially in section, of the configuration of FIG. 2C, wherein the delivery catheter is withdrawn and the stent is fully expanded.

When stent 10 is inserted into a desired location within a patient (as in FIG. 2B), balloon 14 may be inflated, which may thereby expand stent 10 (as in FIG. 2C). At least one strut element 50 of stent 10 may thereby be brought into contact with at least a portion of the surface 40 of the obstruction 42 and/or the inner wall 72 of a vessel 70 (see FIG. 2D). Vessel 70 may be expanded slightly by the expansion of stent 10 to provide volume for the expanded lumen. As a result, interference of blood flow by stent 10 may be minimized, in addition to preventing unwarranted movement of stent 10 once the expansion is complete. It is expressly contemplated that stent 10 may also be self-expanding.

FIG. 3A shows a cross-sectional view of an exemplary stent strut 60 having side surfaces 62, 64 disposed between an outer (or abluminal) surface 66 which can contact body tissue when the stent is implanted, and an inner (or subluminal) surface 68 that is opposite the abluminal surface (i.e. faces the center of the lumen). The surfaces may be substantially planar, or may be substantially contoured. The substantially trapezoidal shape of the strut 60 of FIG. 3A is meant to be exemplary, and other suitable shapes are discussed infra. Generally, abluminal surface 66 of strut 60 may be substantially proximate a lumen wall when the stent is deployed (see infra, FIG. 4A).

FIG. 3B shows a cross-sectional view of an exemplary stent strut 100 having side surfaces 102, 104 disposed between an abluminal surface 106 and a subluminal surface 108. Strut 100 may also have a depression 110 with a support element 112 at least partially disposed therein. Although the depression 110 is shown to be on the abluminal surface 106, it alternatively may be on the subluminal surface 108. In the embodiment shown in FIG. 3B, the cross-sectional shape of depression 110 is substantially rectangular. However, it is expressly contemplated that depression 110 may have, without limitation, a substantially circular, U-shaped, C-shaped, bowl-shaped, triangular, oval-shaped, polygonal, square, or trapezoidal shape. Also, depression 110 may be, without limitation, a groove, slot, basin, concavity, dip, pit, sag, indentation, dimple, bowl, trench, trough, impression, dent, recess, channel, furrow, rut, slit, opening, hole, ditch, gutter, or carved-out volume of the strut that may be suitable for retaining at least a portion of a support element 112. Various shapes, sizes, and arrangements of depressions 110 are shown and described below.

Depression 110 may have substantially smooth surfaces 110a, or at least one surface may be roughened, serrated, grooved, or exhibit some other form of surface texture. It may be beneficial to provide some form of texture on at least one surface 110a of depression 110 to create surface friction between the depression 110 and the support element 112 to more effectively retain the support element 112 in depression 110. Other techniques may be used to retain support element 112 in a depression 110, including, without limitation, adhesives, polymers, welding, press-fitting, magnetism, or interference-fitting.

Support element 112 may be, without limitation, a wire, strand, filament, cable, line, thread, string, tress, fiber, chain, cord, twine, braid, mesh, bar, rod, pole, staff, shaft, stick, rail, lattice, web, net, beam, post, baton, or stake that may be suitable for use with a medical device. Various shapes, sizes, orientations, arrangements, and patterns of support elements 112 are shown and described below.

In the embodiment shown in FIG. 3B, the cross-sectional shape of the support element 112 has a substantially circular cross-sectional shape. However, it is expressly contemplated that support element 112 may have, without limitation, a substantially square, rectangular, triangular, oval-shaped, polygonal, C-shaped, U-shaped, star-shaped, or irregular cross-sectional shape. Various exemplary embodiments of these and other shapes are shown and described below.

Moreover, the support element 112 shown in FIG. 3B is also substantially hollow. Support element 112 may further have pores for retaining a therapeutic agent below the outer surface of the support element. However, it is expressly contemplated that support element 112 may be, without limitation, substantially solid, or entirely solid. Support element 112 may also have a substantially smooth outer surface, or may have a substantially grooved outer surface to increase the surface area of the support element 112. Support element 112 may also be substantially twisted or braided, the result of which may be spaces for retaining a coating composition for controlled elution.

Preferably, support element 112 provides a stent and/or stent strut with added structural support. As shown in the figures herein, a depression 110 may be formed in a strut, the result of which may be a decrease in the strength of that particular strut due to the removal of material to create depression 110. Preferably, support element 112 is comprised of a material, and possesses the requisite mass and/or size, to replace and/or exceed the strength of the strut, as compared to the strut without the depression 110.

Support element 112 is preferably made of a biocompatible material, and more preferably is made of metallic substance, such as nitinol. Preferably, support element 112 is also made of a resilient material or shape memory material. (See infra discussion relating to FIG. 13). Other suitable materials for support element 112 include stainless steel, gold, platinum, tantalum, carbon fibers, titanium, titanium alloys, cobalt alloys, ceramics, and polymers (which may be biostable or bioabsorbable). Support element 112 may be formed from multiple strands of the same material. Support element 112 may also be formed from inductive coiled wire which may be used to create a current to raise the temperature of the support element, and may also be sued to enhance MRI capabilities. Support element 112 may also be comprised of more than one material.

FIG. 3C shows a perspective view of a portion of strut 100 having a cross-section substantially identical to the strut 100 shown in FIG. 3B. As seen in this embodiment, strut 100 has a depression 110 that extends along a length of the strut 100, and at least partially contains a support element 112. It may be preferable, as shown in the embodiments of FIGS. 3B and 3C to have a portion of the support element 112 extending above the plane of abluminal surface 106. This may be beneficial, inter alia, to minimize contact between a lumen/vessel wall and the stent and/or the abluminal surface 106 of strut 100. In the embodiment shown in FIG. 3C, strut 100 has a longitudinal axis X-X. Depression 110 may be substantially parallel to axis X-X (i.e., the depression may not intersect or contact an edge 106a of a surface such as an abluminal surface 106).

Figure 3D:
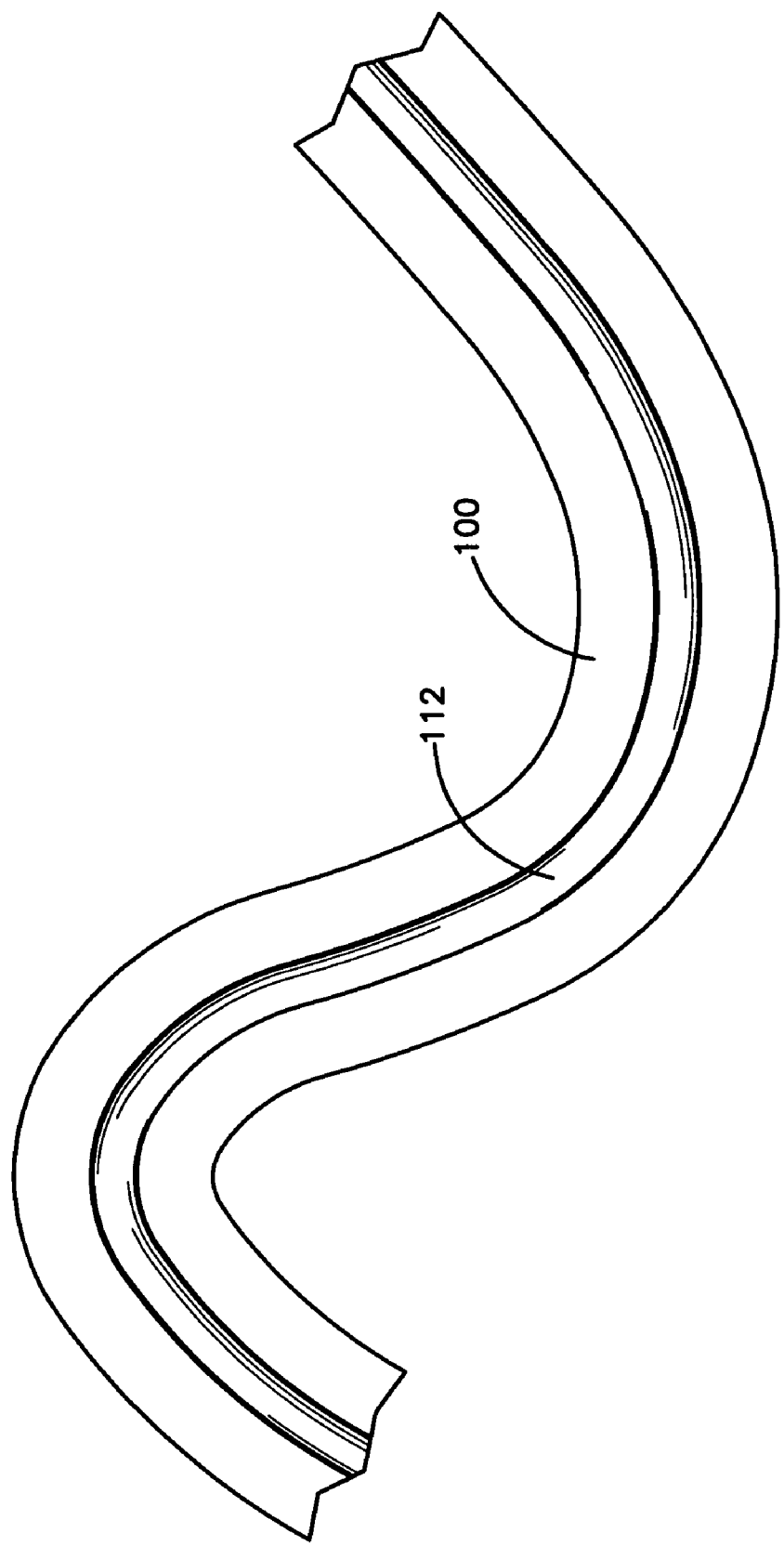
FIG. 3D is a top view of a strut having a support element.

FIG. 3D shows a top view of a portion of strut 100 having a support element 112 extending along a length of the strut. In this embodiment, support element 112 is at least partially disposed in a depression 110 (not shown), and is substantially similar in shape of the strut along at least a portion of its length. Moreover, in this embodiment, support element 112 does not deviate from the shape or contour of strut 100, so as to avoid having a portion of the support element 112 extend into a opening or gap between an adjacent strut 100. It may be beneficial to situate the support element 112 in the manner shown in FIG. 3D to maximize the structural support capabilities (discussed above) that the support element 112 may add to strut 100. It may also be beneficial to not have support element 112 extend into openings or gaps between struts 100 to enable such gaps or openings to be unobstructed in situ, which may be particularly advantageous in bifurcated stent systems, wherein a second stent may be passed through an opening in the sidewall of a first strut.

A comparison of the expanded states of a stent having strut 60 and strut 100 is shown in FIGS. 4A and 4B, respectively. As shown in FIG. 4A, when strut 60 (which does not have a depression or support element, but which may be coated with a therapeutic agent 66a) is proximate the inner wall 72 of a lumen or vessel 70, a portion of abluminal surface 66 of strut 60 may contact the inner wall 72. This may not be preferable for a number of reasons, including the likelihood that any coating 66a on at least the abluminal surface 66 may be rubbed off during expansion of the stent. In contrast, when a stent having strut 100 (with depression and support element) is expanded, shown in FIG. 4B, the outer surface of support element 112 may contact the inner wall 72 of lumen or vessel 70, instead of the abluminal surface 106 of strut 100.

It is also noted that the outer surface of the support element 112 may be shaped so that it is sufficiently sharp or pointed to break-up or crack plaque in a lumen, as may be achieved with a cutting balloon.

In some embodiments, the support element 112 can extend beyond the abluminal surface 106 of a strut 100. The percentage of a support element 112 extending beyond the plane of an abluminal surface 106 of a strut 100 may vary in several ways. The percentage (calculated by the cross-sectional area) of a support element 112 extending beyond an abluminal surface 106, at a specific cross-sectional as seen in FIG. 3B, may be approximately 1%, 5%, 10%, 20%, 30%, 40%, 50%, or more than 50%. Moreover, the percentage (calculated by volume) of a support element 112 extending beyond an abluminal surface 106, over a length of a strut as seen in FIG. 3C, may be approximately 1%, 5%, 10%, 20%, 30%, 40%, 50%, or more than 50%. This percentage may also vary over the length of a support element 112 and strut 100.

While the strut 100, depression 110, and support element 112 shown in FIG. 3C are shown to be of substantially constant dimensions over their respective lengths, it is expressly contemplated that the dimensions of strut 100, depression 110, and/or support element 112 may vary over their respective length. For instance, it may be preferable to have curvilinear depression 110 and support element 112 disposed on a substantially longitudinal strut 100 to increase the gross length of the support element 112 without having to increase the net length of the strut 100. Additionally, it may be preferable to have a depression 110 and/or support element 112 that vary in thickness, area, diameter, shape, and/or size along their respective length. It is also noted that a depression 110 and a support element 112 need not vary concurrently or similarly along the same length of a strut 100. For example, a depression 110 may have a substantially constant size and shape over a length, but the support element 112 therein may have a substantially variable shape and/or size over the same length. Further variations are expressly contemplated and will be appreciated by those of skill in the art.

FIGS. 5A-5H show various embodiments of depressions 110 and abluminal surface 106 variations on a strut 100. These drawings are meant to be exemplary, as further variations are expressly contemplated and will be appreciated by those of skill in the art. The embodiment shown in FIG. 5A has a relatively deep depression (as compared to the embodiment shown in FIG. 3B) such that no portion of the support element 112 extends beyond the plane of abluminal surface 106. This arrangement may be beneficial if support element 112 is coated with a therapeutic agent not intended for direct contact with a body lumen. The embodiment shown in FIG. 5B has a relatively shallow depression such that a relatively large portion of support element 112 extends beyond the plane of the abluminal surface 106. This arrangement may be beneficial if it is desired that, upon expansion of the stent, there is a substantial space between the lumen wall 72 and the abluminal surface 106 (see FIG. 4B). The embodiments shown in FIGS. 5C and 5D have substantially bowl-shaped or curved depressions 110, which may make it easier to insert support element 112 in depression 110 during manufacture.

Figure 5E:
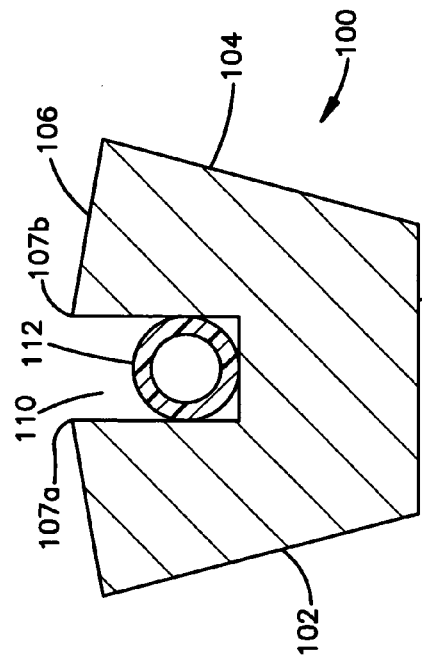
Figure 5F:
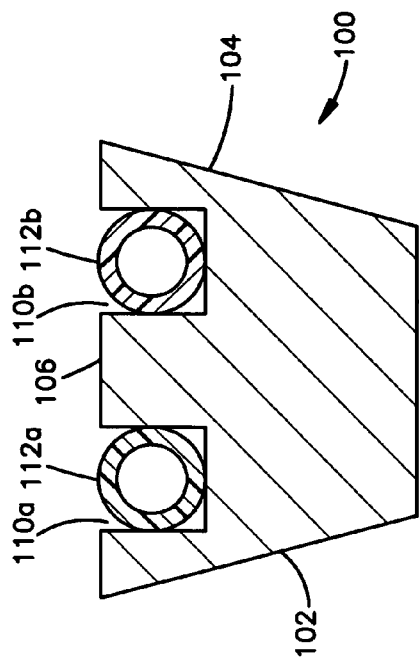
Figure 5G:
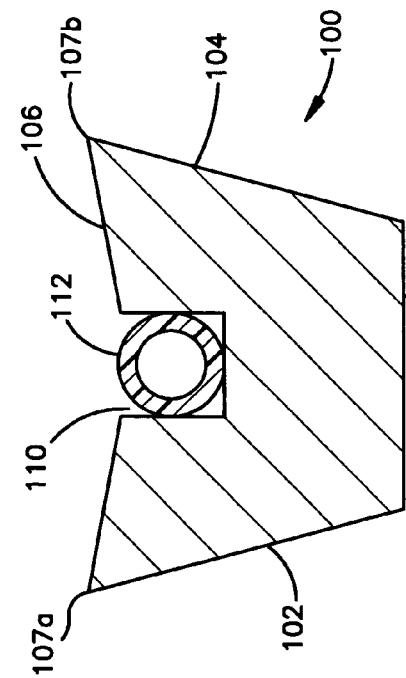
Figure 5H:
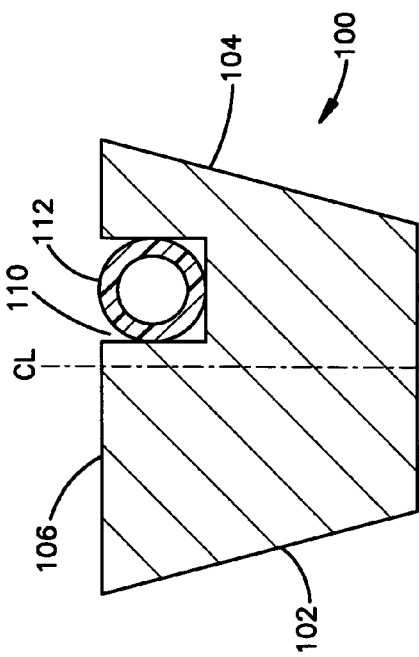

The embodiments in FIGS. 5E and 5F have sloped abluminal surfaces 106, such that when the stent is expanded, apices 107a, 107b may be the only portion of the abluminal surface 106 to contact a lumen wall. These arrangements may be beneficial to minimize contact with a lumen wall, but prevent a support element 112 from directly contacting the lumen wall. Apices 107a, 107b may be cornered or substantially rounded-off. The embodiment in FIG. 5E may also be beneficial to make it easier to insert support element 112 in depression 110 during manufacture. The embodiment shown in FIG. 5G has a depression 110 off-center from centerline CL. This may be beneficial to position a support element 112 on a particular side of a stent to treat an irregularly-shaped target area on a body lumen. The embodiment shown in FIG. 5H has two support elements 112a, 112b in respective depressions 110a, 110b. It is expressly contemplated that a strut 100 may have zero, one, two, three, four, or more than four support elements 112 at a particular location. It is further contemplated that more than one support element 112 may be located in a single depression 110.

FIGS. 6A-6D show further various embodiments of a depression 110 on a strut 100 containing at least a portion of a support element 112. The embodiment in FIG. 6A has a trough-shaped depression 110 having sloped side walls, which may be beneficial to make it easier to insert support element 112 in depression 110 during manufacture. The embodiment in FIG. 6B has a U-shaped depression 110 that closely conforms to the support element 112 therein. This embodiment may be beneficial if it is desirable to maximize the contact area between the inner surface of the depression 110 and the support element 112. This embodiment may also be beneficial if it is desirable to minimize the amount of "wiggle room" or play between the depression 110 and the support element 112. The embodiments in FIGS. 6C-6D show various other depression 110 shapes that may be utilized in conjunction with a support element 112. The embodiments in FIGS. 6A-6D are meant to be exemplary, as further variations are expressly contemplated and will be appreciated by those of skill in the art.

FIG. 7 shows (via an end view) a representative way of how support elements 112 may be placed into depressions 110 on struts 100 during manufacturing. In this case, one or more support elements 112 may be made of a resilient and/or shape memory material, may be expanded around a stent 10 with struts 100 having depressions 110, and thereafter may be released, cooled, pressurized, etc. to compress or contract into the depressions 110. For example, if support element 112 is made of a resilient material, the support element 112 may be stretched around a stent 10, and thereafter released so that support element 112 resiliently compresses into a depression 110. In this sense, a support element 112 may be "snapped-in" to a depression 110.

In the case that support element(s) 112 are not resilient and/or made of a shape memory material, such element(s) 112 may be applied to a strut 100 and/or depression 110 by the methods of affixation described in relation to FIG. 13A. Moreover, support element 112 may comprise a continuous component that is pushed into depressions 110 in a sequential manner starting a first point on a stent, and working circumferentially along the perimeter of the stent to insert the support elements 112 into depressions 110 on consecutive struts 100. Further, support element 112 may comprise a plurality of undulating rings that may be placed into position sequentially along the stent, either by shape-memory or by crimping. An adhesive may be used to fix a support element 112 in a desired location. Various other application methods will be appreciated by those of skill in the art.

It is noted that support element 112 may be a network that is substantially identical in shape to a corresponding network of struts 100 that form at least a portion of a stent. For example, for the stents 10 shown in FIGS. 1A-1C, support element 112 may be substantially the same shape such that it fits into depressions 110 made on the struts 100 that make up stent 10. It is also noted that support elements 112 may be smaller, segmented components, wherein numerous support element 112 are placed on a single stent 10 or strut 100.

As discussed herein, depression(s) 110 may be formed by a variety of methods and materials. In one embodiment, multiple techniques may be used to imprint multiple depressions on a single device. In one embodiment of the present invention, depressions are formed on a coated medical device using a dimethylsiloxane (PDMS) mold with a pattern. In another embodiment, depressions are formed on a strut when the stent is originally made (i.e. the strut is pre-formed to have a depression).

Depressions formed on the stent may be uniform or random. In one embodiment, depressions are uniformly formed on one section of the stent and randomly formed on another section of the stent. In another embodiment, the depressions are uniformly formed over the entire stent. In another embodiment, depressions are randomly imprinted on the stent.

The device may be formed with any shaped depression. The pattern may be smooth, without sharp edges or corners. The depression may be deep or shallow. In one embodiment, the depressions are orthogonal. A depression may be comprised of polygons such as circles, triangles, squares, shapes with regular or irregular sides and angles, or a combination thereof. In another embodiment, depressions comprise three-dimensional polygons.

The surface morphology of the device can be engineered to target a specific location of the body or in order to regulate the rate at which a therapeutic agent is released into the body. For example, in one embodiment, depressions are only formed to a first portion of the medical device. Manipulating surface morphology may also allow for therapeutic agent release rates on the ends of the medical device to be the same as the therapeutic agent release rates in the middle of the medical device. In one embodiment, portions with more depressions may be formed in the middle of the device while more portions with less depressions may be formed on the ends of the device. Since the edge of a device may have more surface area over a given length than a face of the device, this depression formation may keep the therapeutic agent release rate constant.

As discussed herein, various techniques for forming depressions may be utilized. One type of exemplary technique involves removal of material from the strut to form a depression. Examples of such techniques include without limitation fine mechanical or chemical abrading; chemical, laser or mechanical etching, printing, vapor deposition, or lithographic processes.

Suitable lithography techniques may include proximal probe lithography, scanning probe lithography or a combination thereof. In one embodiment of the invention, scanning probe lithography is used for forming depressions in the medical device with features smaller than about 100 nm, 50 nm, 10 nm, 1 nm, or less. In one embodiment, scanning probe lithography is used to form depressions in the medical device with mechanical patterning such as scratching, nano-indentation, or local heating with a sharp tip. In another embodiment, depressions are formed in the stent using dip-pen nanolithography techniques.

Yet another process that may be used to form depressions are embossing techniques. Through recent advances in embossing, even nanoscale depressions can be formed through the embossing technique.

Also suitable for forming depressions are printing techniques. These printing techniques may include, but is not limited to, microcontact printing or inkjet printing, or a combination thereof. The microcontact printing method may use a polydimethylsiloxane (PDMS) or other elastomeric stamp to form the depressions. In one embodiment, the desired depressions can be formed on the stamp using conventional photolithography or another lithography technique. In another embodiment, microcontact printing is used to contemporaneously form depressions on every surface of the medical device that is in contact with the stamp at a given time.

Another process that may be used to form depressions is a molding technique, which may include, but is not limited to, replica molding, microtransfer molding, micromolding capillaries, solvent-assisted micromolding, or a combination thereof.

The molding technique may use a polydimethylsiloxane (PDMS) or other elastomeric stamp to form depressions. In one embodiment, replica molding may be used to efficiently duplicate the information such as shape, morphology, and structure present on the surface of the coating. In another embodiment, replica molding may be used for duplicating two or three dimensional topologies on the coating of a medical device in a single step. Preferably, replica molding may enable the duplication of complex structures in the stamp in multiple copies of the coating with nanoscale resolution in a simple, reliable and inexpensive way. A single implementation of replica molding may be used multiple times on a single medical device, for a single time on the coatings of multiple medical devices, or for a combination thereof.

The size and shape of the stamp may be manipulated by controlled deformation of the stamp used to mold the pattern. By mechanically stretching, bending, compressing or a combination thereof, the surface of the stamp and thereby the pattern on the stent, can be inexpensively and reliably altered.

Depressions 110 may further be formed by material addition using a laser to write/deposit material onto the strut surface 100 to effectively "build up" surrounding material, creating a depression 110 where material is not added, or added in a lesser amount. Depressions 110 may further be formed by laser chemical vapor deposition (LCVD), laser cladding, or by sintering deposited particles of material.

Preferably, support element 112 is coated with a therapeutic agent and/or polymer, with at least a portion of the support element 112 extending over the plane created by the abluminal surface 106 of strut 100 (as described above). Preferably, support element 112 is coated prior to insertion into a depression 110. Support element 112 may be partially or fully coated. The amount of coating applied to a support element 112 may vary over its length, and may also be patterned. The selective coating of support element 112 may be beneficial in at least that complications with a coated strut surface sticking to a expansion balloon may be reduced, as if support element 112 is coated, but the carrying strut 100 is not, an expandable balloon extending along the subluminal surface of the stent may not encounter a coated strut surface. However, it is also expressly contemplated that all or a portion of at least one strut may also be coated, in addition to, or instead of, a support element 112.

Figure 8A:
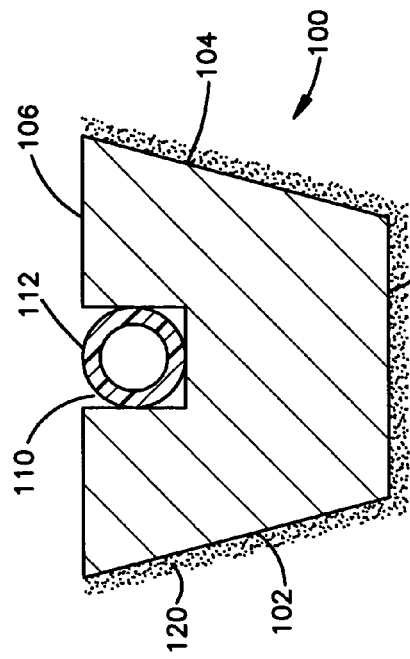
FIGS. 8A-8D are cross-sectional views of various embodiments of struts having a support element, in which the strut is at least partially coated.
Figure 8B:
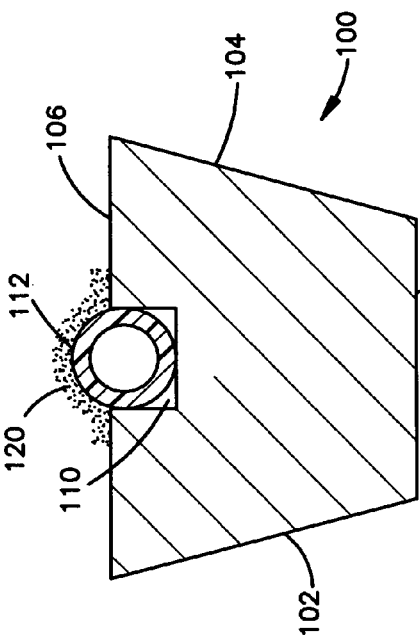
Figure 8C:
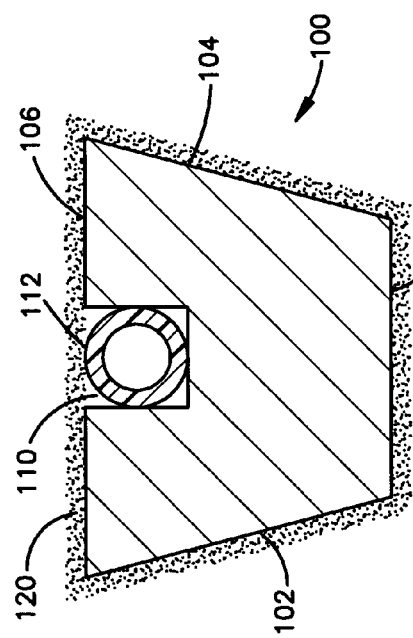
Figure 8D:
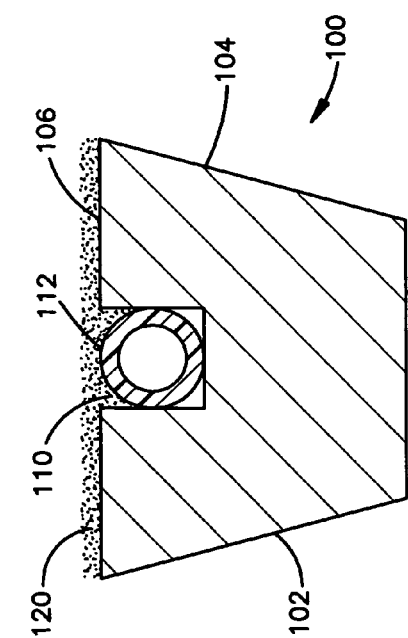

FIGS. 8A-8D show various embodiments of a strut 100 having a depression 110 containing at least a portion of a support element 112, and wherein at least a portion of the strut 100 and/or support element 112 is coated with a coating composition 120. In each of the embodiments shown in FIGS. 8A-8D, support element 112 may be independently coated with a coating prior to insertion into depression 110. In this sense, coating composition 120 may be supplementary to the coating already on support element 112. Coating 120 may be a therapeutic agent, but may also be non-therapeutic. For example, coating 120 may serve to retain support element 112 within depression 110. This may be beneficial if support element 112 is comprised of a non-resilient material. Coating 120 may be substantially dissolvable when implanted in the body. The embodiment in FIG. 8A shows a strut 100 that is fully encapsulated, wherein the coating 120 on the over the top surface 106 of strut 100 does not protrude into the depression 110. The embodiment in FIG. 8B shows a strut 100 having a coating 120 on side surfaces 102, 104 and subluminal surface 108, but wherein abluminal surface 106 is uncoated. This arrangement may be beneficial if it is desirable to release a first therapeutic agent proximate the lumen wall (i.e. coated on the support element 112), and also release a second therapeutic agent at a location away from the lumen wall (i.e. coating 120). The embodiment in FIG. 8C shows a strut 100 coated with a coating 120 only on the abluminal surface 106, and substantially covering depression 110 and support element 112. This arrangement may be beneficial if it is desirable to have a coating 120 containing a first therapeutic agent released prior to the exposure and release of a second therapeutic agent coated on support element 112. The embodiment in FIG. 8D shows a strut 100 having a support element 112 with an additional composition coating 120. This arrangement may be beneficial to protect the therapeutic coating of support element 112 during deployment, especially if support element 112 is coated with a agent that rubs off easily.

It is also contemplated that a coating composition may be stored underneath a support element 112 within a depression 110, such that the coating may seep out of the depression 110 after implantation into the body, but is shielded by the support element 112 during implantation into the body. This may be preferable if a slow elution of a coating (which may comprise a therapeutic agent) is desired.

A coating composition may be prepared, for example, by applying a mixture of a polymeric material, a solvent and a therapeutic agent on a surface to form a coating. If such a composition is used the polymeric material incorporates the therapeutic agent. Alternatively, the coating composition may not include a polymeric material. The following is a description of suitable materials and methods useful in producing a coating on the surface of support elements stent struts of the invention.

Polymeric materials useful for forming the coating should be ones that are biocompatible, particularly during insertion or implantation of the device into the body and avoids irritation to body tissue. Examples of such polymers include, but not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Since the polymer is being applied to a part of the medical device which undergoes mechanical challenges, e.g. expansion and contraction, the polymers are preferably selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. The polymer is selected to allow the coating to better adhere to the surface of the strut when the stent is subjected to forces or stress. Furthermore, although the coating can be formed by using a single type of polymer, various combinations of polymers can be employed.

Generally, when a biologically active material used is a hydrophilic, e.g., heparin, then a matrix material comprising a more hydrophilic material has a greater affinity for the biologically active material than another matrix material that is less hydrophilic. When a biologically active material used is a hydrophobic, e.g., paclitaxel, actinomycin, sirolimus (RAPAMYCIN), tacrolimus, everolimus, and dexamethasone, then a matrix material that is more hydrophobic has a greater affinity for the biologically active material than another matrix material that is less hydrophobic.

Examples of suitable hydrophobic polymers include, but not limited to, polyolefins, such as polyethylene, polypropylene, poly(1-butene), poly(2-butene), poly(1-pentene), poly(2-pentene), poly(3-methyl-1-pentene), poly(4-methyl-1-pentene), poly(isoprene), poly(4-methyl-1-pentene), ethylene-propylene copolymers, ethylene-propylene-hexadiene copolymers, ethylene-vinyl acetate copolymers, blends of two or more polyolefins and random and block copolymers prepared from two or more different unsaturated monomers; styrene polymers, such as poly(styrene), poly(2-methylstyrene), styrene-acrylonitrile copolymers having less than about 20 mole-percent acrylonitrile, and styrene-2,2,3,3,-tetrafluoropropyl methacrylate copolymers; halogenated hydrocarbon polymers, such as poly(chlorotrifluoroethylene), chlorotrifluoroethylene-tetrafluoroethylene copolymers, poly(hexafluoropropylene), poly(tetrafluoroethylene), tetrafluoroethylene, tetrafluoroethylene-ethylene copolymers, poly(trifluoroethylene), poly(vinyl fluoride), and poly(vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly(heptafluoroisopropoxypropylene), and poly(methacrylonitrile); acrylic polymers, such as poly (n-butyl acetate), poly(ethyl acrylate), poly(1-chlorodifluoromethyl)tetrafluoroethyl acrylate, poly di(chlorofluoromethyl)fluoromethyl acrylate, poly(1,1-dihydroheptafluorobutyl acrylate), poly(1,1-dihydropentafluoroisopropyl acrylate), poly(1,1-dihydropentadecafluorooctyl acrylate), poly (heptafluoroisopropyl acrylate), poly 5-(heptafluoroisopropoxy)pentyl acrylate, poly 11-(heptafluoroisopropoxy)undecyl acrylate, poly 2-(heptafluoropropoxy)ethyl acrylate, and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly(ethyl methacrylate), poly(2-ethylhexyl methacrylate), poly(n-hexyl methacrylate), poly(phenyl methacrylate), poly(n-propyl methacrylate), poly(octadecyl methacrylate), poly(1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyesters, such a poly (ethylene terephthalate) and poly(butylene terephthalate); condensation type polymers such as and polyurethanes and siloxane-urethane copolymers; polyorganosiloxanes, i.e., polymeric materials characterized by repeating siloxane groups, represented by $R_a SiO_{4-a/2}$, where R is a monovalent substituted or unsubstituted hydrocarbon radical and the value of a is 1 or 2; and naturally occurring hydrophobic polymers such as rubber.

Examples of suitable hydrophilic monomer include, but not limited to; (meth)acrylic acid, or alkaline metal or ammonium salts thereof; (meth)acrylamide; (meth)acrylonitrile; those polymers to which unsaturated dibasic, such as maleic acid and fumaric acid or half esters of these unsaturated dibasic acids, or alkaline metal or ammonium salts of these dibasic adds or half esters, is added; those polymers to which unsaturated sulfonic, such as 2-acrylamido-2-methylpropanesulfonic, 2-(meth)acryloylethanesulfonic acid, or alkaline metal or ammonium salts thereof, is added; and 2-hydroxyethyl (meth)acrylate and 2-hydroxypropyl(meth) acrylate.

Polyvinyl alcohol is also an example of hydrophilic polymer. Polyvinyl alcohol may contain a plurality of hydrophilic groups such as hydroxyl, amido, carboxyl, amino, ammonium or sulfonyl ($—SO_3$). Hydrophilic polymers also include, but are not limited to, starch, polysaccharides and related cellulosic polymers; polyalkylene glycols and oxides such as the polyethylene oxides; polymerized ethylenically unsaturated carboxylic acids such as acrylic, mathacrylic and maleic acids and partial esters derived from these acids and polyhydric alcohols such as the alkylene glycols; homopolymers and copolymers derived from acrylamide; and homopolymers and copolymers of vinylpyrrolidone.

The coating layer may also contain one or more biological active materials. A biologically active material can also be included in the structural element. The term "biologically active material" encompasses therapeutic agents, such as biologically active agents, and also genetic materials and biological materials. The genetic materials mean DNA or RNA, including, without limitation, of DNA/RNA encoding a useful protein stated below, intended to be inserted into a human body including viral vectors and non viral vectors as well as anti-sense nucleic acid molecules such as DNA, RNA and RNAi. Viral vectors include adenoviruses, gutted adenoviruses, adeno associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, skeletal myocytes, macrophage), replication competent viruses (e.g., ONYX 015), and hybrid vectors. Non viral vectors include artificial chromosomes and mini chromosomes, plasmid DNA vectors (e.g., pCOR), cationic polymers (e.g., polyethyleneimine, polyethyleneimine (PEI)) graft copolymers (e.g., polyether PEI and polyethylene oxide PEI), neutral polymers PVP, SP1017 (SUPRATEK), lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF 1, FGF 2, VEGF, Endotherial Mitogenic Growth Factors, and epidermal growth factors, transforming growth factor and platelet derived endothelial growth factor, platelet derived growth factor, tumor necrosis factor, hepatocyte growth factor and insulin like growth factor), transcription factors, proteinkinases, CD inhibitors, thymidine kinase, and bone morphogenic proteins (BMP's), such as BMP 2, BMP 3, BMP 4, BMP 5, BMP 6 (Vgr 1), BMP 7 (OP 1), BMP 8, BMP 9, BMP 10, BMP 11, BMP 12, BMP 13, BMP 14, BMP 15, and BMP 16. Currently preferred BMP's are BMP 2 BMP 3, BMP 4, BMP 5, BMP 6, BMP 7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono nuclear cells, progenitor cells (e.g., endothelial progenitor cells) stem cells (e.g., mesenchymal, hematopoietic, neuronal), pluripotent stem cells, fibroblasts, macrophage, and satellite cells.

Biologically active material also includes non genetic therapeutic agents, such as:

anti thrombogenic agents such as heparin, heparin derivatives, urokinase, and PPack (dextrophenylalanine proline arginine chloromethylketone);

anti proliferative agents such as enoxaprin, angiopeptin, or monoclonal antibodies capable of blocking smooth muscle cell proliferation, hirudin, acetylsalicylic acid, tanolimus, everolimus, amlodipine and doxazosin;

anti inflammatory agents such as glucocorticoids, betamethasone, dexamethasone, prednisolone, corticosterone, budesonide, estrogen, sulfasalazine, rosiglitazone, mycophenolic acid, and mesalamine;

antineoplastic/antiproliferative/anti miotic agents such as paclitaxel or analogs or derivatives thereof, 5 fluorouracil, cisplatin, vinblastine, vincristine, epothilones, methotrexate, azathioprine, adriamycin and mutamycin; endostatin, angiostatin and thymidine kinase inhibitors, cladribine;

anesthetic agents such as lidocaine, bupivacaine, and ropivacaine;

anticoagulants such as D Phe Pro Arg chloromethyl keton, an RGD peptide containing compound, heparin, antithrombin compounds, platelet receptor antagonists, anti thrombin antibodies, anti platelet receptor antibodies, aspirin (aspirin is also classified as an analgesic, antipyretic and anti inflammatory drug), dipyridamole, protamine, hirudin, prostaglandin inhibitors, antiplatelet agents such as trapidil or liprostin, platelet inhibitors and tick antiplatelet peptides;

vascular cell growth promotors such as growth factors, Vascular Endothelial Growth Factors (FEGF, all types including VEGF 2), growth factor receptors, transcriptional activators, and translational promotors;

DNA demethylating drug such as 5-azacytidine, which is also categorized as a RNA or DNA metabolite that inhibit cell growth and induce apoptosis in certain cancer cells;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol lowering agents; vasodilating agents; and agents which interfere with endogenous vasoactive mechanisms;

antioxidants, such as probucol;

antibiotic agents, such as penicillin, cefoxitin, oxacillin, tobranycin, rapamycin (sirolimus);

angiogenic substances, such as acidic and basic fibrobrast growth factors, estrogen including estradiol (E2), estriol (E3) and 17 Beta Estradiol;

smooth muscle cell proliferation inhibitors, such as rapamycin; and drugs for heart failure, such as digoxin, beta blockers, angiotensin converting enzyme (ACE) inhibitors including captopril and enalopril, statins and related compounds;

macrolides such as sirolimus, or everolimus or tacrolimus; and other suitable therapeutic agents include halofuginone, inhibitors of HSP 90 protein such as geldanamycin, microtubule stabilizing agents such as epothilone D, and phosphodiesterase inhibitors such as cilostrazole.

Preferred biologically active materials include anti proliferative drugs such as steroids, vitamins, and restenosis inhibiting agents. Preferred restenosis inhibiting agents include microtubule stabilizing agents such as paclitaxel, paclitaxel analogues, derivatives, and mixtures thereof. For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl)glutamine, and 2'-O-ester with N-(dimethylaminoethyl)glutamide hydrochloride salt.

Other preferred biologically active materials include nitroglycerin, nitrous oxides, nitric oxides, antibiotics, aspirins, digitalis, estrogen derivatives such as estradiol and glycosides.

The solvent that is used to form the coating composition include ones which can dissolve the polymer into solution and do not alter or adversely impact the therapeutic properties of the therapeutic agent employed. Examples of useful solvents include tetrahydrofuran (THF), methyl ethyl ketone chloroform, toluene, acetone, issoctane, 1,1,1-trichloroethane, isopropanol, IPA and dichloromethane or mixtures thereof.

In one method of forming the aforementioned coatings, a coating composition is applied to the surface. Coating compositions can be applied by any method to a surface of a medical device to form a coating layer. Examples of suitable methods include, but are not limited to, spraying such as by conventional nozzle or ultrasonic nozzle, dipping, rolling, electrostatic deposition, and a batch process such as air suspension, pan coating or ultrasonic mist spraying. Also, more than one coating method can be used to make a medical device. Coating compositions suitable for applying a coating to the devices of the present invention can include a polymeric material dispersed or dissolved in a solvent suitable for the medical device, wherein upon applying the coating composition to the medical device, the solvent is removed. Such systems are commonly known to the skilled artisan.

A coating of a medical device of the present invention may include multiple coating layers. For example, the first layer and the second layer may contain different therapeutic agents. Alternatively, the first layer and the second layer may contain an identical therapeutic agent having different concentrations. In one embodiment, either of the first layer or the second layer may be free of therapeutic agent. For example, when the therapeutic solution is applied onto a surface and dried (the first layer), a coating composition free of a therapeutic agent (the second layer) can be applied over the dried therapeutic agent.

Figure 9A:
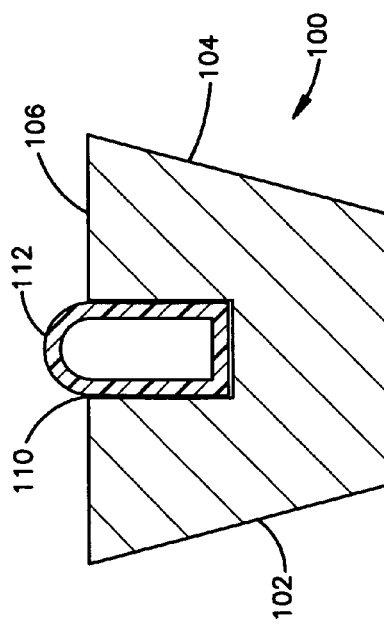
FIGS. 9A-9D are cross-sectional views of various embodiments of struts having a support element having various cross-sectional shapes.
Figure 9B:
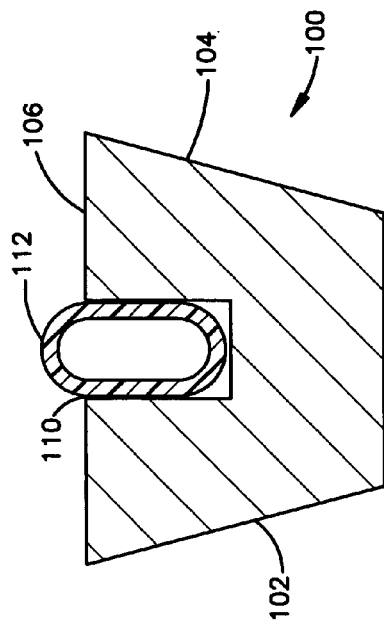
Figure 9C:
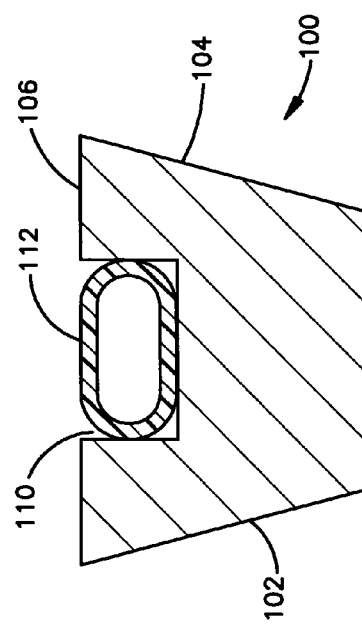
Figure 9D:
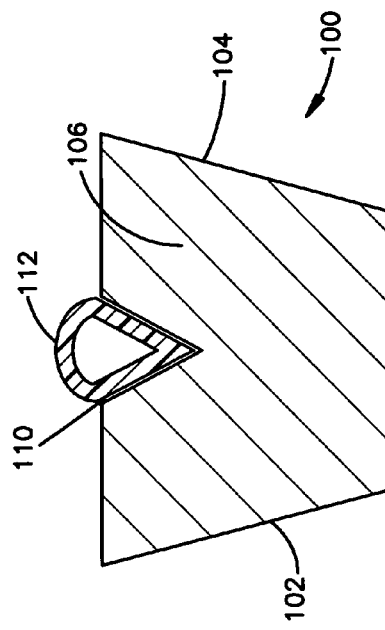

FIGS. 9A-9D show various embodiments of struts 100 having a variety of shaped depressions 110 with shaped support elements 112 therein. The embodiments in FIGS. 9A-9D are meant to be exemplary, as further variations are expressly contemplated. The embodiment in FIG. 9A shows a support element 112 with a rectangular portion disposed in depression 110, and a curved portion protruding out of depression 110. This shape combination may be beneficial to create a tighter fit between rectangular depression 110 and support element 112, yet expose a rounded or curved portion of a support element 112, which may be beneficial to make support element 112 more atraumatic. The embodiments in FIGS. 9B and 9C show support elements 112 having substantially oval-shaped cross-sections disposed in depressions 110. The relatively deep depression 110 in FIG. 9B may be beneficial to create a more secure fit of support element 112 in strut 100. The relatively wide depression 110 and support element 112 of FIG. 9C may be beneficial to expose a greater surface area of support element 112 to a lumen wall. The embodiment in FIG. 9D shows a similar embodiment to that of FIG. 9A, except that the lower portion of support element 112 is substantially triangular to create an "ice cream cone"-shaped support element 112.

As seen in FIGS. 10A-10D, it is further contemplated that at least one support element 112 may be disposed on any or all surfaces of a strut 100. The location of a support element 112 on a strut 100 may be based on such factors as the desired release of a therapeutic agent, the ease of manufacture, the shape and/or size of the stent, the shape and/or size of the strut, the overall strut pattern of the stent, the desired flexibility of the stent, and the length, shape, and/or size of the support element 112. The embodiment of FIG. 10A shows support element 112 disposed in a depression 110 along the subluminal surface 108 of the strut 100. This may be beneficial if it is desirable to release the therapeutic agent on support element 112 subluminally. The embodiment of FIG. 10B shows a support element 112 disposed in a depression 110 along a side surface 102 of the strut 100. The embodiment of FIG. 10C shows a support element 112a disposed in a depression 110a along the abluminal surface 106 of the strut 100, and another support element 112b disposed in a depression 110b along the subluminal surface 108 of the strut 100. This arrangement may be beneficial when it is desirable to release a first therapeutic agent abluminally via support element 112a, and a second therapeutic agent subluminally via support element 112b. The embodiment of FIG. 10D shows a support element 112a disposed in a depression 110a along the abluminal surface 106 of the strut 100, and another support element 112b disposed in a depression 110b along a side surface 102 of the strut 100.

As shown in FIGS. 11A-11D, it is also contemplated that the use of a depression 110 having a support element 112 therein may be suitable for a variety of strut 100 cross-sectional shapes. For example, the strut 100 cross-sectional shape may be substantially square (FIG. 11A), substantially circular (FIG. 11B), substantially polygonal (FIG. 11C), or substantially oval-shaped (FIG. 11D). Various other shapes are expressly contemplated, and will be appreciated by those of skill in the art. The shape, size, and/or location of depression 110 may vary with the shape of the strut 100.

FIGS. 12A-12D show top views of the abluminal surfaces 106 of strut 100 sections, and the support element(s) 112 disposed in depression(s) (not shown) extending along the length thereof. As shown in FIG. 3C, support element 112 may be substantially longitudinal along a section of a strut 100. However, various other patterns and configurations may be beneficial, depending at least partially on the amount of contact area, if any desired between the support element 112 and a lumen wall, the flexibility of the stent and/or support element 112, the material of the stent and/or support element 112, the amount of therapeutic agent coated on the support element 112, the length of the strut and/or stent, the pattern of the strut, and the overall strut pattern of the stent. For example, the embodiment in FIG. 12A shows a substantially wavy support element 112 extending along a substantially longitudinal strut 100. This configuration may be beneficial to increase the amount of contact area and/or therapeutic agent release from a support element 112 along a strut 100 segment. These benefits may also present in the embodiment of FIG. 12B, which shows a bent support element 112. As shown in FIG. 12C, a strut 100 segment may have intermittent or discontinuous support elements 112a, 112b disposed along it's length. Although not specifically shown in FIG. 12C, it may be beneficial to have numerous, intermittent support elements 112 when a strut segment is substantially wavy, curved, or contoured, thus making it difficult to fit a single support element 112 in a depression 110 disposed thereon. FIG. 12D shows an embodiment of a braided support element 112, which again may be beneficial to increase the amount of contact area and/or therapeutic agent release from a support element 112 along a strut 100 segment. Various other patterns and configurations are expressly contemplated, and will be appreciated by those of skill in the art.

It is further contemplated that a strut 100 may have at least one support element 112 without having a depression 110. As shown in FIGS. 13A-13B, support element 112 is disposed on the abluminal surface 106 of a strut 100. Support element 112 may be affixed to abluminal surface 106 by the methods described above in relation to the retention of a support element 112 within a depression 110. This embodiment may be beneficial or preferred if strut is comprised of a material that makes it difficult to form a depression 110 therein. This embodiment may further be beneficial if it is desirable to selectively place numerous support elements 112a, 112b at various locations along a strut 100 (see top view in FIG. 13B) without regard to where depressions 110 have been formed. This embodiment may even further be beneficial because it eliminates possible concerns over difficulties encountered during manufacture when attempting to fit a support element 112 into a depression 110, and further eliminates the possibility that a support element 112 may not fit properly in a depression 110. It is contemplated that a single stent may have strut segments with support element(s) 112 disposed in a depression 110, and other strut segments with support element(s) 112 not disposed in a depression, as shown in FIGS. 13A-13B.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

What is claimed is:

1. An implantable stent comprising:
a stent sidewall having a plurality of struts including a first strut having an abluminal surface, a subluminal surface, and at least one side surface, the abluminal surface having a width and a length, the width being less than the length;

a first depression formed in the abluminal surface of the first strut, the first depression having a width less than the width of the abluminal surface; and a first support element at least partially disposed in the first depression;

wherein the first support element at least partially comprises a metal filament and wherein the first support element comprises a shape-memory metal; and the stent further comprising a second depression formed in the subluminal surface of the first strut; and a second support element at least partially disposed in the second depression, and wherein the second support element at least partially comprises a metal filament.

2. The stent of claim 1, wherein at least a portion of the first support element extends beyond the abluminal surface of the first strut.

3. The stent of claim 1, wherein the first depression is a groove.

4. The stent of claim 1, wherein the first support element comprises a coating composition disposed thereon and wherein the coating composition comprises a therapeutic agent.

5. The stent of claim 4, wherein the coating composition further comprises a polymer.

6. The stent of claim 1, wherein the first support element has a curved cross-section.

7. The stent of claim 1, wherein the first strut comprises a coating composition disposed thereon.

8. The stent of claim 7, wherein the coating composition comprises a therapeutic agent.

9. The stent of claim 1, further comprising a second strut having an abluminal surface and a third depression formed in the abluminal surface of the second strut.

10. The stent of claim 1, wherein the first support element comprises a resilient metal.

11. The stent of claim 1, wherein the first support element comprises nitinol.

12. The stent of claim 1, wherein the stent is an intravascular stent.

13. An implantable stent comprising:

a plurality of first struts, each first strut having an abluminal surface, a subluminal surface, at least one side surface, and a longitudinal axis, the abluminal surface of each first strut having a first depression formed therein, wherein the first depression is disposed substantially parallel to the longitudinal axis of the first strut; and a plurality of first support elements, each first support element comprising a filament, each first support element having a longitudinal axis, wherein each first support element is at least partially disposed in a first depression of one of the plurality of first struts so that the longitudinal axis of the first support element is substantially parallel to the longitudinal axis of the first strut, and wherein each first support element comprises a shape-memory metal;

at least one of the plurality of first struts further comprising a second depression formed in the subluminal surface; and a second support element at least partially disposed in the second depression.

14. The stent of claim 13, wherein at least a portion of at least one of the plurality of first support elements extends beyond the abluminal surface of the first strut.

15. The stent of claim 13, wherein the first depression is a groove.

16. The stent of claim 13, wherein at least one of the plurality of first support elements comprises a coating composition disposed thereon and wherein the coating composition comprises a therapeutic agent.

17. The stent of claim 13 wherein at least one of the plurality of first support elements has a curved cross-section.

18. The stent of claim 13, wherein at least one of the plurality of first struts comprises a coating composition disposed thereon.

19. The stent of claim 18, wherein the coating composition comprises a therapeutic agent.

20. The stent of claim 13, further comprising a second strut having an abluminal surface and a third depression formed in the abluminal surface of the second strut.

21. The stent of claim 13, wherein at least one of the plurality of first support elements comprises a resilient metal.

22. The stent of claim 13, wherein at least one of the plurality of first support elements comprises nitinol.

23. The stent of claim 13, wherein the stent is a intravascular stent.

24. An implantable stent comprising:

a stent sidewall, the stent sidewall having a plurality of struts and a plurality of openings, wherein, the sidewall comprises a first strut having an abluminal surface, a subluminal surface, and at least one side surface;

a first depression formed in the abluminal surface of the first strut; and a first support element at least partially disposed in the first depression, wherein the first support element does not extend into any of the plurality of openings, and wherein the first support element comprises a shape-memory metal;

wherein the first support element is hollow and wherein a therapeutic agent is disposed within the first support element.

25. The stent of claim 24, wherein at least a portion of the first support element extends beyond the abluminal surface of the first strut.

26. The stent of claim 24, wherein the first depression is a groove.

27. The stent of claim 24, wherein the first support element comprises a coating composition disposed thereon and wherein the coating composition comprises a therapeutic agent.

28. The stent of claim 27, wherein the coating composition further comprises a polymer.

29. The stent of claim 24, wherein the first support element has a curved cross-section.

30. The stent of claim 24, wherein the first strut comprises a coating composition disposed thereon.

31. The stent of claim 30, wherein the coating composition comprises a therapeutic agent.

32. The stent of claim 24, further comprising a second depression formed in the subluminal surface of the first strut; and a second support element at least partially disposed in the second depression.

33. The stent of claim 32, wherein the second support element does not extend into any of the plurality of openings.

34. The stent of claim 24, further comprising a second strut having an abluminal surface and a second depression formed in the abluminal surface of the second strut.

35. The stent of claim 34, further comprising a second support element at least partially disposed in the second depression, and at least partially comprising a metal filament, wherein the second support element does not extend into any of the plurality of openings.

36. The stent of claim 24, wherein the first support element comprises a resilient metal.

37. The stent of claim 24, wherein the first support element comprises nitinol.

38. The stent of claim 24, wherein an outer surface of the first support element defines a plurality of pores.

39. The stent of claim 24, further comprising a first coating, the first coating disposed in the first depression underneath the first support element.

40. The stent of claim 24, wherein the first depression has a first surface, the first surface being textured.

41. A stent comprising:
- a plurality of first struts, each first strut having a first surface, the first surface having a width and a length, the width being less than the length;
- the first surface of each first strut having a first depression formed therein, the first depression having a width less than the width of the first surface; and
- a plurality of first support elements, each first support element being disposed in a first depression of one of the plurality of first struts, wherein each first support element comprises a shape memory metal;
- wherein at least one of the plurality of first support elements being hollow and wherein a therapeutic agent is disposed within the at least one of the plurality of first support elements.

42. The stent of claim 41, the first depression having a depth, each first support element having a height, wherein the depth of the first depression is less than the height of the first support element disposed therein.

43. The stent of claim 41, the first depression having a depth, each first support element having a height, wherein the depth of the first depression is greater than the height of the first support element disposed therein.

44. The stent of claim 41, the first depression having a first surface, the first surface of the first depression being textured.

45. The stent of claim 41, at least one of the plurality of first support elements having a coating.

46. The stent of claim 41, the first depression having a cross-sectional shape, each first support element having a cross-sectional shape, at least a portion of the cross-sectional shape of the first support element being the same as the cross-sectional shape of the first depression in which the first support element is disposed.

47. The stent of claim 41, the first depression having a cross-sectional shape, each first support element having a cross-sectional shape different than the cross-sectional shape of the first depression in which the first support element is disposed.

48. An implantable stent comprising:
- a stent sidewall, the stent sidewall having a plurality of struts and a plurality of openings,
- wherein, the sidewall comprises a first strut having an abluminal surface, a subluminal surface, and at least one side surface;
- a first depression formed in the abluminal surface of the first strut; and
- a first support element at least partially disposed in the first depression, wherein the first support element does not extend into any of the plurality of openings, and wherein the first support element comprises a shape-memory metal; and the stent
- further comprising a second depression formed in the subluminal surface of the first strut; and a second support element at least partially disposed in the second depression.

49. The stent of claim 48, wherein the second support element does not extend into any of the plurality of openings.

* * * * *